(12) United States Patent
Bonde et al.

(10) Patent No.: US 8,954,162 B2
(45) Date of Patent: Feb. 10, 2015

(54) MEDICAL DEVICE IMPLANTATION

(75) Inventors: Eric H. Bonde, Minnetonka, MN (US); Martin T. Gerber, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 2399 days.

(21) Appl. No.: 11/739,982

(22) Filed: Apr. 25, 2007

(65) Prior Publication Data
US 2008/0269716 A1     Oct. 30, 2008

(51) Int. Cl.
| A61M 31/00 | (2006.01) |
| A61B 17/34 | (2006.01) |
| A61N 1/05 | (2006.01) |
| A61N 1/36 | (2006.01) |
| A61B 17/06 | (2006.01) |
| A61B 17/00 | (2006.01) |

(52) U.S. Cl.
CPC .......... *A61N 1/0526* (2013.01); *A61B 17/3468* (2013.01); *A61N 1/0551* (2013.01); *A61N 1/36071* (2013.01); *A61B 2017/06052* (2013.01); *A61B 17/06109* (2013.01); *A61B 2017/00946* (2013.01)
USPC ................... 607/116; 607/1; 607/2; 607/115; 607/118

(58) Field of Classification Search
USPC ........... 607/1–2, 115–116, 118; 604/500, 506
IPC ......... A61N 1/05,1/36, 1/37; A61M 2210/0693, A61M 31/00; A61B 17/3468, 18/1492, 2017/0094, 5/6868, 5/6882
See application file for complete search history.

(56) References Cited

U.S. PATENT DOCUMENTS

| 4,141,365 A | 2/1979 | Fischell et al. |
| 4,512,351 A | 4/1985 | Pohndorf |
| 4,808,157 A | 2/1989 | Coombs |
| 5,255,691 A | 10/1993 | Otten |
| 5,443,492 A | 8/1995 | Stokes et al. |

(Continued)

FOREIGN PATENT DOCUMENTS

| EP | 0278937 A2 | 8/1988 |
| EP | 1 048 270 A1 | 11/2000 |

(Continued)

OTHER PUBLICATIONS

Ishigooka et al., "A new technique for sacral nerve stimulation: a percutaneous method for urinary incontinence caused by spinal cord injury," British Journal of Urology, vol. 81, No. 2, pp. 315-318 (1998).

(Continued)

*Primary Examiner* — Deborah Malamud
(74) *Attorney, Agent, or Firm* — Shumaker & Sieffert, P.A.

(57) ABSTRACT

The disclosure is directed to a method for implanting a medical device proximate to a target tissue site within an occipital region of a patient, such as proximate to an occipital nerve or a trigeminal nerve. The method comprises introducing an implant tool into a patient to define an insertion path to the target tissue site. The implant tool includes a shape memory cannula and a malleable needle at least partially disposed within an inner lumen of the cannula. The shape of the needle may be changed to accommodate different anatomical structures/features of the patient. Upon withdrawal of the needle from the cannula, the cannula may change shape, thereby changing the shape of the insertion path.

23 Claims, 16 Drawing Sheets

(56) References Cited

U.S. PATENT DOCUMENTS

| | | | |
|---|---|---|---|
| 5,562,695 A | 10/1996 | Obenchain | |
| 5,669,882 A | 9/1997 | Pyles | |
| 5,899,909 A | 5/1999 | Claren et al. | |
| 6,104,957 A | 8/2000 | Alo et al. | |
| 6,249,707 B1 | 6/2001 | Kohnen et al. | |
| 6,360,750 B1 | 3/2002 | Gerber et al. | |
| 6,553,264 B2 | 4/2003 | Redko et al. | |
| 6,587,733 B1 | 7/2003 | Cross, Jr. et al. | |
| 6,847,849 B2 | 1/2005 | Mamo et al. | |
| 6,941,171 B2 | 9/2005 | Mann et al. | |
| 6,971,393 B1 | 12/2005 | Mamo et al. | |
| 6,978,180 B2 * | 12/2005 | Tadlock | 607/46 |
| 6,999,819 B2 | 2/2006 | Swoyer et al. | |
| 2002/0147485 A1 | 10/2002 | Mamo et al. | |
| 2003/0028147 A1 | 2/2003 | Aves et al. | |
| 2003/0045919 A1 | 3/2003 | Swoyer et al. | |
| 2003/0171644 A1 | 9/2003 | Anderson et al. | |
| 2003/0176875 A1 | 9/2003 | Anderson et al. | |
| 2003/0212305 A1 | 11/2003 | Anderson et al. | |
| 2004/0193228 A1 | 9/2004 | Gerber | |
| 2004/0210209 A1 * | 10/2004 | Yeung et al. | 604/500 |
| 2004/0210245 A1 | 10/2004 | Erickson et al. | |
| 2005/0010237 A1 | 1/2005 | Niazi | |
| 2005/0033372 A1 | 2/2005 | Gerber | |
| 2005/0055063 A1 | 3/2005 | Loeb et al. | |
| 2005/0070969 A1 | 3/2005 | Gerber | |
| 2005/0096667 A1 | 5/2005 | Smith et al. | |
| 2005/0159797 A1 * | 7/2005 | Chandran et al. | 607/99 |
| 2005/0240238 A1 | 10/2005 | Mamo et al. | |
| 2005/0267555 A1 | 12/2005 | Marnfeldt et al. | |
| 2006/0015131 A1 | 1/2006 | Kierce et al. | |
| 2006/0058575 A1 | 3/2006 | Zaddem et al. | |
| 2006/0089633 A1 | 4/2006 | Bleich et al. | |
| 2006/0095079 A1 | 5/2006 | Gerber | |
| 2006/0129101 A1 | 6/2006 | McGuckin, Jr. | |

FOREIGN PATENT DOCUMENTS

| | | |
|---|---|---|
| EP | 1 048 271 A2 | 11/2000 |
| EP | 1 342 454 A1 | 9/2003 |
| FR | 2 688 407 | 9/1993 |
| WO | WO 00/33909 | 6/2000 |
| WO | WO 2005/032650 | 4/2005 |
| WO | WO 2005/105201 | 11/2005 |
| WO | WO 2005/118057 | 12/2005 |
| WO | 2007087190 A2 | 8/2007 |

OTHER PUBLICATIONS

Abrams et al., "The role of neuromodulation in the management of urinary urge incontinence," British Journal of Urology International, vol. 91, No. 4, pp. 355-359 (2003).

Spinelli et al., "New Percutaneous Technique of Sacral Nerve Stimulation Has High Initial Success Rate: Preliminary Results," European Urology, vol. 43, No. 1, pp. 70-74 (2003).

U.S. Appl. No. 11/338,611, filed Jan. 24, 2006, entitled "Transobturator Lead Implantation for Pelvic Floor Stimulation," by Siegel et al.

U.S. Appl. No. 11/740,049, filed Apr. 25, 2007, entitled "Implant Tool to Facilitate Medical Device Implantation," by Bonde et al.

U.S. Appl. No. 11/740,079, filed Apr. 25, 2007, entitled "Cannula Configured to Deliver Test Stimulation," by Bonde et al.

Office Action dated Aug. 21, 2009 for U.S. Appl. No. 11/338,611 (7 pgs.).

Responsive Amendment dated Nov. 23, 2009 for U.S. Appl. No. 11/338,611 (13 pgs.).

Communication Pursuant to Article 94(3) EPC from counterpart European Patent Application No. 08 733 120.3-1506, dated Feb. 25, 2014, 3 pp.

Response to European Examination Report dated Feb. 25, 2014, from counterpart European Patent Application No. 08733120.3-1506, filed Jul. 2, 2014, 3 pp.

Examination Report from counterpart European Patent Application No. 08733120.3, mailed Nov. 22, 2012, 8 pp.

Response to Examination Report dated Nov. 22, 2012, from counterpart European Patent Application No. 08733120.3, dated May 28, 2013, 7 pp.

* cited by examiner

MEDICAL DEVICE IMPLANTATION

TECHNICAL FIELD

The invention relates to medical devices and, more particularly, methods for implanting medical devices.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, or obesity. The electrical stimulation system may also be used for muscle stimulation, such as for function electrical stimulation of muscles. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, sacral nerve, peripheral nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals.

Electrical stimulation of a peripheral nerve, such as an occipital nerve, may be used to mask a patient's feeling of pain with a tingling sensation, referred to as paresthesia. Occipital nerves, such as a lesser occipital nerve, greater occipital nerve or third occipital nerve, exit the spinal cord at the cervical region, extend upward and toward the sides of the head, and pass through muscle and fascia to the scalp. Pain caused by an occipital nerve, e.g. occipital neuralgia, may be treated by delivering stimulation therapy to the occipital region via an implanted stimulation lead or by delivering drug therapy to the occipital region via an implanted catheter.

SUMMARY

In general, the invention relates to methods for implanting a medical device, such as a medical lead or a fluid delivery conduit, proximate to a target tissue site within an occipital region of a patient. The occipital region may be, for example, proximate to an occipital nerve or a trigeminal nerve. During the implantation procedure, an implant tool comprising a malleable needle and shape memory cannula defines an insertion path through tissue of the patient for the medical device. The malleability of the needle enables the implant tool to change shape (e.g., from substantially straight to curvilinear, or between various curvilinear shapes) and adapt to various anatomical structures of a patient to define an insertion path that is suitable and personalized for the particular patient and target tissue site. For example, a clinician may change the shape (or configuration) of the needle to conform to an anatomical structure of a patient, such as a transverse contour of the neck, which may help increase the precision and accuracy of the implantation procedure.

The cannula that is disposed at least partially around the needle remains within the insertion path after the needle is removed from the patient. The cannula is sized to receive the medical device. The cannula comprises a shape memory material, which permits it to change from a first shape to a second shape upon withdrawal of the needle.

Prior to withdrawing the needle from the patient or implanting the medical device in the patient, the position of the implant tool relative to the target tissue site may be established. In one embodiment, electrical stimulation is delivered to the patient via the needle or at least one electrode on the needle or cannula in order to assess the efficacy of stimulation and/or to determine whether the implant tool is properly positioned relative to the target tissue site.

In one embodiment the invention is directed toward a method comprising introducing an implant tool into a patient, where the implant tool comprises a malleable needle and a cannula disposed around at least a portion of the needle. The cannula comprises a shape memory material. The method further comprises advancing the needle to a target tissue site proximate to at least one of an occipital nerve or a trigeminal nerve of the patient, the needle defining a path through tissue of the patient, and withdrawing the needle from the path. The cannula remains at least partially within the path and changes from a first shape to a second shape after the needle is removed.

In another embodiment, the present invention is directed toward a method comprising introducing an implant tool into a patient via an entry point, where the implant tool comprises a cannula comprising a shape memory material, and a malleable needle disposed at least partially in an inner lumen of the cannula. A distal tip of the needle extends past a distal end of the cannula. The method further comprises advancing the distal tip of the needle to a target tissue site proximate to at least one of an occipital nerve or a trigeminal nerve of the patient, where the distal tip of the needle defines a path from the entry point to the target tissue site, changing a first shape of the needle, and withdrawing the needle from the path. The cannula remains at least partially within the path and changes from the first shape of the needle to a second shape upon withdrawal of the needle from the path.

In another embodiment, the present invention is directed toward a method comprising introducing an implant tool into a patient superior to a fascia layer, the implant tool comprising a cannula comprising a shape memory material and a malleable needle disposed at least partially in an inner lumen of the cannula. A distal tip of the needle extends past a distal end of the cannula. The method further comprises advancing the distal tip of the needle to a target tissue site proximate to at least one of an occipital nerve or a trigeminal nerve of the patient, the distal tip of the needle defining a path through tissue of the patient, withdrawing the needle from the path, and introducing a medical device into the cannula. Upon withdrawal of the needle from the path, the cannula remains at least partially within the path and changes from a first shape to a second shape.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
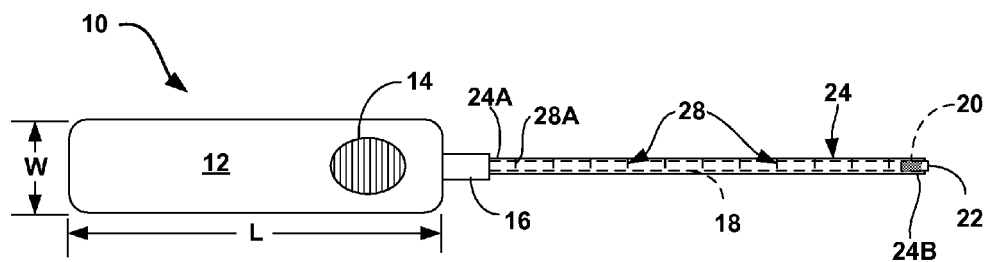
FIGS. 1A and 1B are plan and side views, respectively, of an exemplary implant tool that includes a malleable needle and a shape memory cannula.
Figure 1B:
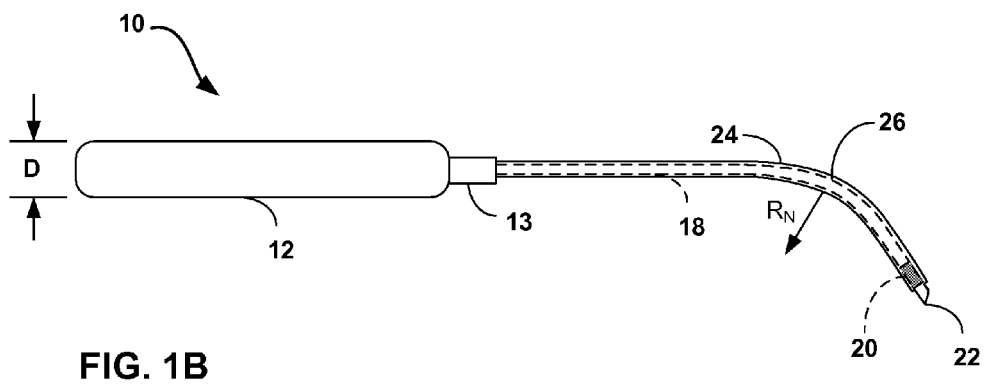

FIGS. 1A and 1B are plan and side views, respectively, of implant tool 10, which includes handle 12, thumb rest 14, neck 16, needle 18 (shown in phantom lines), electrode 20, tip 22, and cannula 24, which is sized to receive needle 18. Implant tool 10 facilitates the implantation of a medical device at an implant site (also known as a target tissue site) within an occipital region of a patient. For example, the clinician may use implant tool 10, and in particular, needle 18 to define an insertion path for the medical device from an entry point at an exterior surface (e.g., the skin or scalp) of the patient to a target tissue site to implant a medical device proximate to an occipital nerve or a trigeminal nerve. Features of implant tool 10 described below, such as malleable needle 18, may help minimize the number of attempts to locate a target tissue site, which may reduce the trauma to tissue and the patient.

The type of medical device implanted into the patient with the aid of implant tool 10 may vary for different therapeutic applications. In some embodiments, the medical device may be an electrical stimulation lead or lead extension that is used to deliver electrical stimulation to a target tissue site and/or sense one or more physiological parameters, e.g., blood pressure, temperature, or electrical activity, of a patient. Hence, in various embodiments, the lead may carry stimulation electrodes, sensing electrodes and/or sensor devices. In another embodiment, medical device may be a fluid conduit, such as a catheter, which is placed to deliver a fluid, such as pharmaceutical agents, pain relieving agents, gene therapy agents or the like from a fluid delivery device, such as a fluid reservoir and/or pump, to a target tissue site in a patient. The fluid conduit may also be used to withdraw a fluid from a target tissue site in a patient. Thus, in some embodiments, "therapy" may include stimulation therapy, sensing or monitoring of one or more physiological parameters, fluid delivery, fluid withdrawal, and the like. "Target tissue site" refers generally to the target site for implantation of a medical device, regardless of the type of therapy. Implant tool 10 may be used to facilitate implantation of any medical device that is used to deliver therapy to a tissue site in a patient.

Handle 12 is ergonomically shaped for easy handling by a clinician. In the embodiment shown in FIGS. 1A-1B, handle 12 is generally rectangular with curved edges. In other embodiments, handle 12 may be formed in a cylindrical, spherical, or other ergonomic shape designed to be held by one hand. A generally cylindrical handle 12 shape may useful in some cases because of its symmetry. A clinician's grip on handle 12 may be substantially the same despite the relative orientation of handle 12, which may allow the clinician to easily direct needle 18 to any location within a patient without regard to the orientation of handle 12. A cylindrical handle shape may also allow the clinician to easily manipulate implant tool 10 when attempting to position needle 18 near an occipital nerve, trigeminal nerve or other tissue site within the occipital region of a patient.

Handle 12 may be provided in different sizes to accommodate differently sized hands of varying clinicians. In addition, handle 12 may be made to accommodate use in a right or left hand, either as ambidextrous or separate models. In one embodiment, handle 12 has a length L in a range of approximately 10 centimeters (cm) to approximately 30 cm, a width W in a range of approximately 1 cm to approximately 10 cm, and a depth D in a range of approximately 0.5 cm to approximately 5 cm. For example, handle 12 may have a length L in a range of approximately 10 cm to approximately 15 cm, a width W in a range of approximately 2 cm to approximately 4 cm, and a depth D in a range of approximately 1 cm to approximately 3 cm.

Handle 12 may be constructed of an injection moldable plastic such as polystyrene, polypropylene, polycarbonate, or any other polymer. In some embodiments, handle 12 may be constructed of a metal alloy including stainless steel or aluminum or a composite material. The material used to construct handle 12 may be dependent on the intended life of implant tool 10. For example, a disposable handle 12 may require an inexpensive plastic material, while a reusable handle 12 may require a more durable metal material. In addition to these materials, ergonomic rubber or similar material may be added to handle 12 to increase ease of use of implant tool 10.

Handle 12 is shaped to allow a clinician to hold it with one hand. Thumb rest 14 is also provided to facilitate manipulation of implant tool 10 by a clinician. Thumb rest 14 may be constructed of a soft rubber, plastic or an elastomeric material other than rubber to provide comfort and friction between the thumb of a clinician and handle 12. That is, thumb rest 14 may help prevent the clinician's thumb from slipping during a medical device implantation procedure. Other ergonomic features of handle 12 may be provided as well. For example, the sides of handle 12 may follow the contours of a hand or fingers. In addition, soft or rubber pads may be placed where handle 12 contacts the clinician's hand to provide a secure griping surface.

In some embodiments, implant tool 10 may be completely disposable to eliminate possible contamination between different patients. In other embodiments, one or more components of implant tool 10 may be reusable to reduce equipment costs. For example, handle 12 may be reusable as it may not come into contact with the patient. Handle 12 may be sterilized in the event that biological tissues come into contact with the handle. Needle 18 may be detachable and disposable. Alternatively, needle 18 may be autoclaved or chemically sterilized for use in implanting a lead into a different patient.

Neck 16 securely attaches needle 18 to handle 12. Neck 16 may provide an attachment mechanism to enable needle 18 to be removed from neck 16. Detachment of needle 18 may be desirable if needle 18 is to be separately disposable or sterilized from handle 12. Alternatively, neck 16 may be permanently attached to needle 18, but removable from handle 12. As yet another alternative, handle 12, neck 16, and needle 18 may be an integral unit.

Needle 18 may be any object that is introduced into or otherwise penetrates tissue of a patient. Needle 18 may be formed from a metal alloy such as stainless steel, aluminum or Nitinol. Needle 18 is malleable, which allows needle 18 to achieve different curvatures. That is, needle 18 is rigid enough to traverse through tissue without unintentionally changing shape, while still being capable of being shaped or formed upon the application of sufficient force to needle 18. The force needed to change the shape of needle 18 exceeds the force typically exerted on the needle during introduction into tissue and guidance through the tissue. In some embodiments, needle 18 is composed at least in part of stainless steel, although other materials may also be used.

In some cases, the shape of needle 18 may be modified to facilitate placement of a medical device proximate various target tissue sites within a patient. A clinician may manipulate needle 18 during an implantation procedure to achieve different curvatures as necessary to reach a target tissue site within the patient. For example, the clinician may grasp needle 18 and apply a force to change the shape of needle 18. The malleability of needle 18 may allow the clinician to more easily, and without substantially damaging surrounding tissue, advance needle 18 to an implant site than would be possible with a straight needle or a needle having a predefined curve. The clinician may manipulate needle 18 to conform to an anatomical structure of a patient, such as a transverse contour of the neck of a patient, to reduce trauma caused during implantation of the medical device within the patient. In this way, implant tool 10 is suitable for use in an implantation procedure in which needle 18 traverses an anatomical structure that may vary in shape from one patient to another. The clinician may change the shape of needle 18 while needle 18 is partially disposed within the patient. For example, the clinician may partially withdraw needle 18 from the patient prior to changing the shape of needle 18. Alternatively, the clinician may withdraw the entire needle 18 and cannula 24 assembly from the patient prior to changing the shape of needle 18.

In the embodiment shown in FIGS. 1A and 1B, needle 18 is curved in one plane. However, needle 18 is malleable, and may be shaped to curve outside of one plane to facilitate insertion of needle 18 into different regions within the head of the patient to access different target tissue sites within the occipital region of the patient. In one particular example, needle 18 is substantially solid and initially curved at bend point 26 to facilitate traversal around different anatomical features of the patient, such as to facilitate traversal around an ear. However, during implantation within the patient, the clinician may adjust the curvature of needle 18 to achieve a curvilinear shape other than the one shown in FIG. 1B by grasping needle and bending (or flexing) needle 18 into the desired shape.

Tip 22 of implant tool 10 may be percutaneously introduced into tissue of a patient or tip 22 may be introduced through an incision. Tip 22 is used to pierce tissue and create a tunnel through tissue of the patient. In some embodiments, tip 22 is not sharp enough to pierce nerves or vasculature, which adds a degree of safety to the medical device implantation procedure. Tip 22 may be shaped similar to a wedge, cone, pyramid, or any other shape that includes decreased surface area at the distal end of needle 18 to define a sharp point. An electrically conductive electrode 20 may be located near or on tip 22 for test stimulation during placement of needle 18. Electrode 20 may be formed on needle 18 or cannula 24 using any suitable fabrication technique, such as deposition, crimping or welding. Electrode 20 may be cylindrical, circular, or rectangular in shape. In other embodiments, needle 18 or cannula 24 may include multiple electrodes, such as to simulate a quad or octad lead and allow testing a quad or octad lead prior to implantation of the lead. Alternatively, the entire needle 18 may be electrically conductive. In this case, the majority of needle 18 may be covered with an electrically insulative coating or sleeve. Alternatively, cannula 24 placed over needle 18 may be electrically insulative.

Electrode 20 and/or an electrically conductive tip 22 of needle 18 may also be useful for locating nerves that are to be avoided during the implantation of the medical device. A relatively low frequency pulse may be applied to electrode 20 and/or distal tip 22 as needle 18 is advanced to the target tissue site. The low frequency pulse may depolarize nerves that are close to electrode 20 and/or tip 22, resulting in a compound muscle action potential on the innervated muscle. The clinician may monitor the muscle or muscle group while advancing implant tool 10 through tissue in order to determine whether needle 18 is passing too close to the nerve to be avoided.

Hence, an electrode may be formed at tip 22 of needle 18 and coupled to an electrical conductor within needle 18, or the entire needle 18 may be electrically conductive, in which case an insulative coating, sleeve or cannula 24 defines the size and length of the electrode at the tip 22 of needle 18. In each case, the insulative coating, sleeve or cannula 24 limits stimulation energy to a small electrode area at the distal end of needle 18. In some other embodiments, an insulative coating, sleeve or cannula 24 may define one or more window-like apertures that expose selected portions of the needle 18 to define one or more electrode regions either at distal tip 22 or displaced some distance from distal tip 22.

In some embodiments, needle 18 is hollow and open at tip 22. A hollow needle 18 may allow the inclusion of a visualization scope to enable the clinician to view interior regions within the patient at tip 22 or permit the flow of a fluid to the tissue to lubricate or anesthetize the surrounding tissue or reduce tissue damage and/or to dilate (i.e., separate) the tissue layers along the insertion path of needle 18. If needle 18 is hollow, a stylet may be introduced into needle 18 during tissue tunneling in order to help prevent tissue coring.

Needle 18 may vary in length. Differently sized patients may require different sizes of needle 18. In general, the length of needle 18 may be in a range of approximately 2 cm to approximately 40 cm. For example, in one embodiment, needle 18 may have a length of approximately 5 cm to approximately 15 cm, or in another embodiment, approximately 9 cm to approximately 20 cm. In some embodiments, needle 18 may have a diameter of approximately 1 millimeter (mm) to approximately 10 mm. For example, in one embodiment, needle 18 may have a diameter of approximately 1 mm to approximately 5 mm. Needle may have a radius of curvature $R_N$ about bend point 26 in a range of approximately 1 cm to 20 cm. In one embodiment, the radius of curvature $R_N$ about bend point 26 is approximately 5 cm to 15 cm, to permit ease of insertion to the desired tissue site Needle 18 may be constructed of a metal alloy with a strength and stiffness great enough to resist substantial bending upon insertion within tissue of the patient. As mentioned above, such metals may include stainless steel, aluminum or Nitinol. In some embodiments, a plastic material may be used to construct needle 18. If a plastic material is used, an electrical conductor may be provided within needle 18 for conduction of stimulation energy to an electrode formed at or adjacent to distal tip 22 of needle 18. In some cases, the configuration of needle 18 may be changed by a clinician.

Figure 2A:
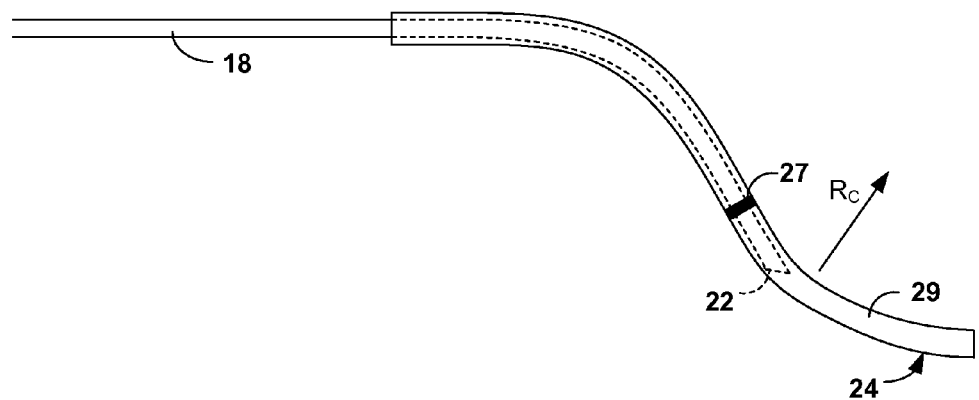
FIG. 2A illustrates an exemplary shape of the cannula shown in FIGS. 1A-B with the needle partially withdrawn from the cannula.

In FIGS. 1A and 1B, needle 18 is received within an inner lumen of cannula 24, which partially covers an outer surface of needle 18 as needle 18 is tunneled through tissue. Upon reaching the target tissue site within a patient, needle 18 may be withdrawn from cannula 24. FIG. 2A illustrates needle 18 of implant tool 10 partially removed from inner lumen 29 of cannula 24. Cannula 24 is of sufficient length that cannula 24 may extend from a target stimulation site within an occipital region of a patient through the entry point, such that a portion of cannula 24 is outside of the patient. Inner lumen 24 has a sufficient diameter to receive a lead or other medical device.

Cannula 24 may also include visible markers 28 that are detectable by imaging techniques, such as fluoroscopic imaging or x-ray imaging. In other embodiments, markers 28 may be visible without the aid of imaging techniques. For example, markers 28 may be printed markings (e.g., lines, text or graphical symbols) on cannula 24, an indentation in cannula 24 or another type of marker that is visible or otherwise detectable (e.g., detectable by a radiographic device) by the clinician. Markers 28 may be helpful for determining the relative depth of implant tool 10 relative to an outer surface of a patient or a target tissue site when inserting needle 18 and cannula 24 within the patient. For example, marker 28A near proximal end 24A of cannula 24 may remain visible to the clinician as clinician guides needle 18 and cannula 24 into a patient, thus indicating the approximate depth of distal tip 22 of needle 18 as well as the distal end 24B of cannula 24. In addition, after needle 18 is removed from cannula 24, the clinician may observe markers 28 to determine whether cannula 24 has inadvertently been withdrawn from the patient or to determine the approximate depth of distal end 24B of sheath 24 within the patient. The clinician may, for example, locate a marker 28 with respect to skin of the patient. In some embodiments, needle 18 may also include one or more visible markers.

Cannula 24 may serve as a medical device introducer once needle 18 is removed from the patient. Cannula 24 is flexible to permit it to assume the shape of needle 18 while needle 18 is disposed within inner lumen 29. As cannula 24 is placed over needle 18, for example, cannula 24 assumes a first shape, i.e., the shape of needle 18. However, cannula 24 is constructed of a flexible material comprising a shape memory, which enables cannula 24 to change shape once needle 18 is removed from its inner lumen 29. A shape memory material may be any material, such as a metal alloy or plastic, which "remembers" its geometry. One type of shape memory material shapes from a first shape to a second during heating or at a higher temperature. The "memory" properties of the material may be attributable to a temperature-dependent martensitic phase transformation from a low-symmetry to a highly symmetric crystallographic structure. Another type of shape memory material is a pseudo-elastic or superelastic material that may be retained in a first shape via a force that is applied to the shape memory material (e.g., needle 18 inserted inside cannula 24), and changes to a second shape upon removal of the force.

Examples of suitable shape memory materials include, but are not limited to, a copper-zinc-aluminium alloy, copper-aluminium-nickel alloy, a nickel-titanium alloy (e.g., Nitinol) or ethylene tetrafluoroethylene (ETFE). Cannula 24 may be constructed of other plastics capable of being thermoset, or heated to a certain shape. Nitinol may provide an additional benefit in that it may be more readily visualized during fluoroscopy.

As shown in FIG. 2A, as needle 18 is removed from cannula 24, cannula 24 changes conformation to a second shape. The second shape may aid in directing a distal tip of a medical lead, catheter or another medical device to an appropriate nerve site, as well as aid in fixation of the medical lead, catheter or other medical device. The second shape is formed in the material of cannula 24, and assumes a radius of curvature $R_C$. $R_C$ may vary due to patient anatomy or nerve targeted to be stimulated. In general, $R_C$ is in a range of approximately 1 cm to 20 cm. More preferably, $R_C$ is in a range of approximately 2 cm to 10 cm. As needle 18 is completely removed from cannula 24, cannula 24 remains in the second shape shown in FIG. 2A. A medical device may then be introduced into the inner lumen of cannula 24 previously occupied by needle 18 of implant tool 10.

Cannula 24 may include an additional visible marker 27 to indicate the direction in which cannula 24 is configured to curve. Marker 27 enables the clinician to orient implant tool 10 during implantation in the patient such that when needle 18 is removed from inner lumen 29 of cannula 24, cannula 24 curves in the desired direction. In some embodiments, marker 27 is in a location in which marker 27 remains visible to the clinician after the clinician introduces implant tool 10 into the patient. For example, marker 27 may be positioned on handle 12 in addition to or instead of on cannula 24. In general, marker 27 may be located anywhere on tool 10, so long as marker provides the clinician with enough information to determine which direction cannula 24 will curve. Marker 27 may be differentiated from visible markers 28 by, for example, being a different color, shape, length or any other means of differentiation that allows a clinician to easily distinguish between marker 27 and markers 28.

Cannula 24 may also help refine the shape of the insertion path previously defined by needle 18. In some cases, needle 18 may not be able completely define the desired insertion path because the shape (i.e., configuration) of needle 18 is dictated by the shape that is necessary to reach the target tissue site without causing substantial damage to tissue. For example, in some embodiments, it may be desirable for a deep portion of the insertion path (i.e., the portion furthest from the entry point) to pivot or curve about 30 degrees or more. However, it may be undesirable for the distal portion of needle 18 to pivot about 30 degrees or more because such a needle may be difficult to guide through tissue of the patient without causing unnecessary trauma to the tissue. Cannula 24, on the other hand, may provide the pivot or curve after being tunneled through the tissue.

The pivot or curve at the end of the insertion path may be useful for implanting a lead, catheter or another elongated medical device to be implanted with extra slack in order to impart strain relief to the implanted elongated medical device. That is, upon changing shape after the removal of needle 18, cannula 24 may refine the insertion path to include a greater curvature than that achieved by needle 18, which allows an elongated medical device to be implanted such that the elongated member has a greater length than necessary to reach the implant site of an electrical stimulator, fluid delivery device or another therapy device to be implanted. As described in further detail below, the greater length of the elongated medical device may help the medical device withstand pulling forces attributable to the movement of muscles along the path traversed by the elongated medical device. The shape memory aspect of cannula 24 may also aid in the implantation of a medical device to regions within a patient that may be difficult to reach with malleable needle 18, which may not be able to achieve to certain radii of curvature.

In addition to the shape memory material of cannula 24, a coating may also be applied to cannula 24. For example, a parylene or oxide film coating may be applied to cannula 24 in order to electrically insulate the cannula. Also, addition of a lubricating film or coating, such as PTFE, to the outer surface of cannula 64 may be desirable to facilitate insertion.

Figure 2B:
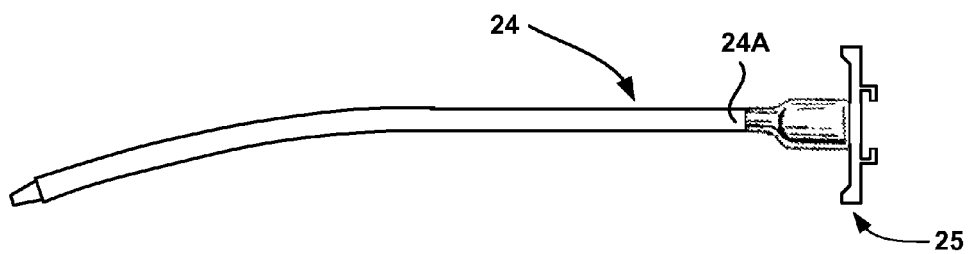
FIG. 2B illustrates an embodiment of a cannula that includes a luer lock hub.

In addition, cannula 24 may include a luer lock hub 25, as shown in FIG. 2B, to provide a feature for attaching to a syringe or another fluid delivery device to inject local anesthesia or another fluid into tissue for pain control during the medical device implantation procedure. Luer lock hub 25 may also be used to delivery a fluid to dilate (i.e., separate) the tissue layers to improve subcutaneous dissection and steerability of needle 18 and catheter 24. Luer lock hub 25 may be attached to proximal end 24A of cannula 24 after needle 18 is withdrawn from cannula 24. In some embodiments, hub 25 may also provide a handle for the clinician to grasp and manipulate cannula 24 after needle 18 is removed from cannula 24. Alternatively, cannula 24 may include another type of handle, such as one similar to handle 12, and which is configured to mate with handle 12 so that needle 18 and cannula 24 may "mate" together to define a substantially unitary implant tool.

Figure 3:
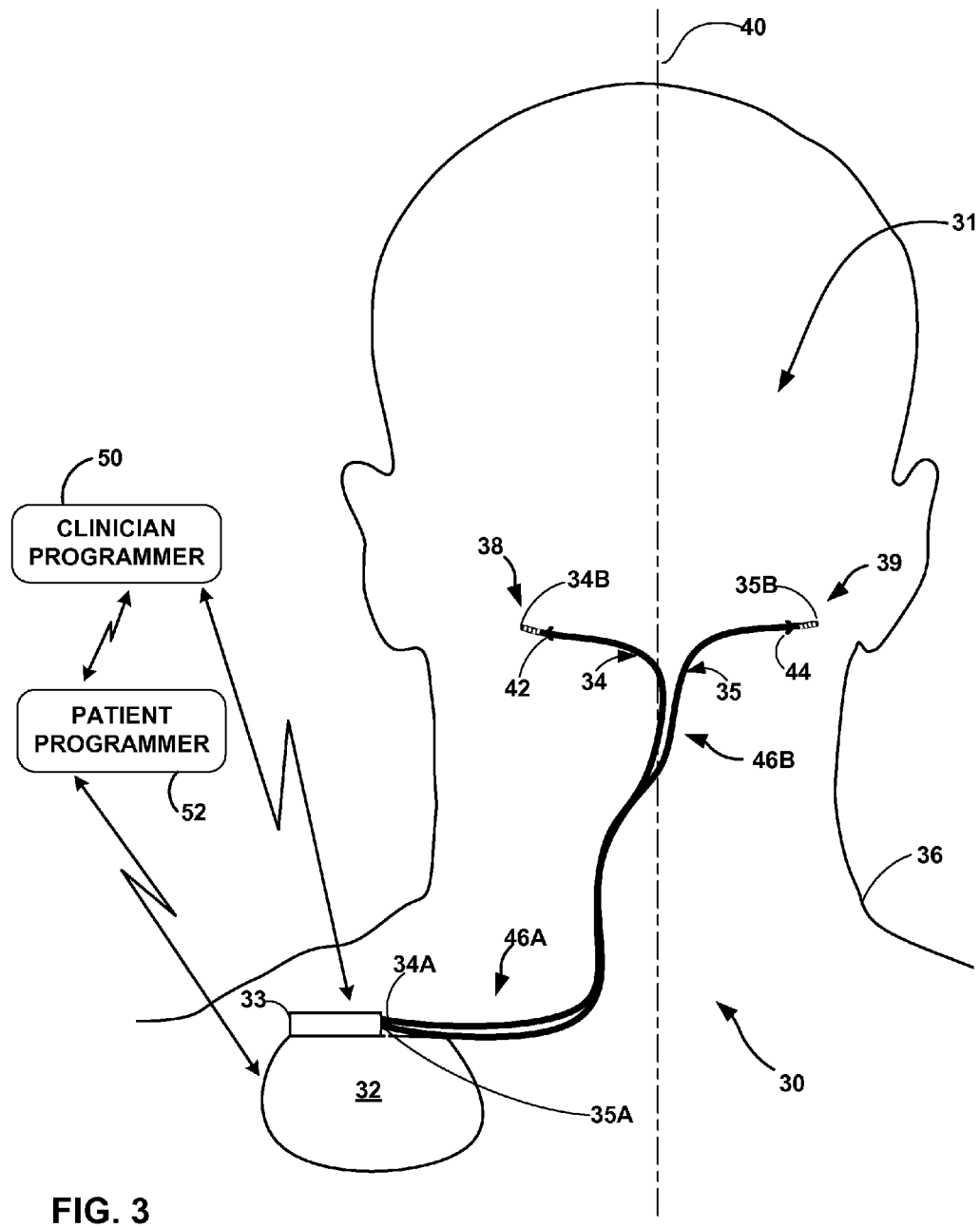
FIG. 3 is a schematic diagram of a therapy system, which includes an electrical stimulator coupled to two stimulation leads that have been implanted in a body of a patient proximate to two target tissue sites in an occipital region of the patient's head.

FIG. 3 is a schematic diagram of therapy system 30, which includes electrical stimulator 32 coupled to stimulation leads 34 and 35, which have been implanted using implant tool 10 of FIGS. 1A-2A. In the example of FIG. 1, electrical stimulator 32 is implanted in patient 36 proximate to target stimulation sites 38 and 39. In one embodiment, target stimulation sites 38 and 39 are within an occipital region 31 within patient 36. Occipital region 31 generally encompasses occipital nerve sites and trigeminal nerve sites of patient 36, which may be, for example, an occipital nerve (e.g., a greater occipital nerve, lesser occipital nerve, third occipital nerve), a trigeminal nerve, tissue adjacent to the trigeminal or occipital nerves, or a nerve branching from the occipital and/or trigeminal nerves. Thus, reference to an "occipital nerve" or a "trigeminal nerve" throughout the disclosure also includes branches of the occipital and trigeminal nerves, respectively. In addition, the therapy may be delivered to both an occipital nerve and trigeminal nerve by a single therapy system 30. Stimulation of the occipital region 31 may help alleviate pain associated with, for example, chronic migraines, cervicogenic headaches, occipital neuralgia or trigeminal neuralgia.

Electrical stimulator 32 provides a programmable stimulation signal (e.g., in the form of electrical pulses or substantially continuous-time signals) that is delivered to target stimulation sites 38 and 39 by implantable medical leads 34 and 35, respectively, and more particularly, via stimulation electrodes carried by leads 34 and 35. Electrical stimulator 32 may also be referred to as a pulse or signal generator, and in the embodiment shown in FIG. 1, electrical stimulator 32 may also be referred to as a neurostimulator. In some embodiments, lead 34 and/or lead 35 may also carry one or more sense electrodes to permit neurostimulator 32 to sense electrical signals or other physiological parameters (e.g., blood pressure, temperature, etc.) from target stimulation site 38 and/or 39, respectively.

Proximal ends 34A and 35A of leads 34 and 35, respectively, may be both electrically and mechanically coupled to connection ports of connector block 33 of neurostimulator 32 either directly or indirectly (e.g., via a lead extension). Conductors disposed in the lead body of each of leads 34 and 35 may electrically connect stimulation electrodes (and sense electrodes, if present) adjacent to distal ends 34B and 35B of leads 34 and 35, respectively, to neurostimulator 32.

In the embodiment of therapy system 30 shown in FIG. 1, target stimulation sites 38 and 39 are located within the patient's head, such as proximate to one or more occipital nerves, and on opposite sides of midline 40 of patient 36. When therapy system provides electrical stimulation therapy to occipital nerves of patient 36, leads 34 and 35 may be implanted at the back of the head of patient 36, as shown in FIG. 1. When therapy system 30 is used for stimulating a trigeminal nerve, target stimulation sites 38 and 39 may be on the side or front of the head of patient 36. Midline 40 is a schematic representation of the line that divides patient 36 into approximately equal and symmetrical left and right halves. Delivering therapy to two target tissue sites, such as sites 38 and 39, may be used to deliver therapy to two nerve branches that branch from the same nerve. Nerves may branch into left and right branches that extend to opposite sides of midline 40, and therapy is delivered to two nerve branches on opposite sides of midline 40 (such as at target tissue sites 38 and 39). Stimulation of two nerve branches on opposite sides of midline 40 may be referred to as bilateral stimulation. However, bilateral stimulation may also refer to stimulation of any two regions of patient 36 either sequentially, simultaneously or otherwise. Delivering therapy after nerves branch, e.g., closer to the nerve endings, may allow more targeted therapy delivery with fewer side effects.

Therapy system 30, however, is useful in other neurostimulation applications. Thus, in alternate embodiments, target stimulation sites 38 and 39 may be at locations proximate to any other suitable nerve in body of patient 36, which may be selected based on, for example, a therapy program selected for a particular patient. For example, in other embodiments, therapy system 30 may be used to deliver neurostimulation therapy to other areas of the nervous system, in which cases, leads 34 and 35 would be implanted proximate to the respective nerve(s). As one example, leads 34 and 35 may be implanted proximate to other nerves and/or structures of the head and neck of patient 36.

Accurate lead placement may affect the success of occipital nerve stimulation. If lead 34 and/or lead 35 is located too deep, i.e., anterior, in the subcutaneous tissue, patient 36 may experience muscle contractions, grabbing sensations, or burning. Such problems may additionally occur if lead 34 and/or lead 35 migrate after implantation. Furthermore, if leads 34 and 35 are implanted at the back of the neck of patient 36, leads 34 and 35 may be subjected to pulling and stretching that may increase the chances of lead migration. For these reasons, leads 34 and 35 may include one or more fixation elements 42 and 44, respectively, to help prevent migration.

In the illustrated embodiment, leads 34 and 35 include tine-like fixation elements 42 and 44, respectively, which are configured to engage with surrounding tissue to substantially fix a position of leads 34 and 35. Fixation elements 42 and 44 may be expanded or activated by any suitable means. In some embodiments, fixation elements 42 and 44 may be restrained or otherwise prevented from premature fixation by cannula 24 or another mechanism prior to introduction into patient 36.

For example, fixation elements 42 and 44 may be configured to fold inward toward the outer surface of leads 34 and 35, respectively, upon insertion in cannula 24. Upon implantation into patient 36, fixation elements 42 and 44 may be expanded or activated by active or passive means. For example, in embodiments in which fixation elements 42 and 44 are tine-like structures, they may be expandable by elastic force such that fixation elements 42 and 44 automatically expand upon removal of the restraint mechanism. Alternatively, fixation elements 42 and 44 may be expanded by mechanical force, such as by pulling leads 34 and 35, respectively, in a proximal direction after implantation in patient 36, such that when fixation elements 42 and 44 engage with surrounding tissue, fixation elements 42 and 44 expand outward.

Although fixation elements 42 and 44 are shown to be tine-like elements in the embodiment of FIG. 1, in other embodiments, fixation elements 42 and 44 may each be any suitable actively or passively deployed fixation element that helps prevent migration of leads 34 and 35 when leads 34 and 35 are implanted in patient 36, such as, but not limited to, one or more barbs, hooks, wire-like elements, adhesives (e.g., surgical adhesives), balloon-like fixation elements, tissue receiving cavities, pinning fixation elements, collapsible or expandable fixation structures, and so forth. In addition, fixation elements 42 and 44 may be formed in situ (i.e., after leads 34 and 35 are implanted in patient 36), such as by delivering a solidifying material (e.g., an adhesive or a hardenable structure material) to one or more exit ports along one or more surface of lead 34 and/or 35 to form fixation elements that extend from lead 34 and/or 35 to engage with surrounding tissue. Fixation elements 42 and 44 may be composed of any suitable biocompatible material, including, but not limited to, polymers, titanium, stainless steel, Nitinol, other shape memory materials, hydrogel or combinations thereof.

In some embodiments, fixation elements 42 and 44 are attached directly to leads 34 and 35. However, in other embodiments, fixation elements 42 and 44 may not be attached directly to leads 34 and 35, but may be carried by another apparatus that is attached to the leads 34 and 35, such as a sleeve or mounting band. An example of a mounting band is described in commonly-assigned U.S. Pat. No. 6,999,819, entitled "IMPLANTABLE MEDICAL ELECTRICAL STIMULATION LEAD FIXATION METHOD AND APPARATUS" and issued on Feb. 14, 2006.

In the illustrated embodiment, neurostimulator 32 is implanted in the back of patient 36 over the trapezius muscle (e.g., electrical stimulator 32 may be disposed within a surgically formed subcutaneous pocket formed near the trapezius muscle). Neurostimulator 32 may be inserted into patient 36 at incision site 46A. Leads 34 and 35 may also be inserted into patient 36 at incision site 46A and advanced to target tissue sites 38 and 39, respectively, with implant tool 10 that includes a curved introducer needle 18 and shape memory cannula 24. In this manner, neurostimulator 32, lead 34, and lead 35 may all be inserted using a single incision at incision site 46A. Alternatively, leads 34 and 35 may be advanced to a second incision site 46B with implant tool 10. In some cases, the clinician may find it desirable to further manipulate and position leads 34 and 35 relative to target tissue sites 38 and 39 via second incision site 46B. In alternative embodiments, neurostimulator 32 may be implanted at other suitable locations within patient 36, such as but not limited to, in a pectoral region, lower back, lower abdomen, or buttocks of patient 36. The location at which the stimulator 32 is implanted may vary according to the health, condition or anatomy of patient 36.

Therapy system 30 also may include a clinician programmer 50 and a patient programmer 52. Clinician programmer 50 may be a handheld computing device that permits a clinician to program neurostimulation therapy for patient 36, e.g., using input keys and a display. For example, using clinician programmer 50, the clinician may specify stimulation parameters for use in delivery of electrical stimulation therapy. Clinician programmer 50 supports telemetry (e.g., radio frequency telemetry) with neurostimulator 32 to download neurostimulation parameters and, optionally, upload operational or physiological data stored by neurostimulator 32. In this manner, the clinician may periodically interrogate neurostimulator 32 to evaluate efficacy and, if necessary, modify the stimulation parameters.

Like clinician programmer 50, patient programmer 52 may be a handheld computing device. Patient programmer 52 may also include a display and input keys to allow patient 36 to interact with patient programmer 52 and neurostimulator 32. In this manner, patient programmer 52 provides patient 36 with an interface for control of neurostimulation therapy by neurostimulator 32. For example, patient 36 may use patient programmer 52 to start, stop or adjust neurostimulation therapy. In particular, patient programmer 52 may permit patient 36 to adjust stimulation parameters such as duration, amplitude, pulse width and pulse rate, within an adjustment range specified by the clinician via clinician programmer 52, or select from a library of stored stimulation therapy programs.

Neurostimulator 32, clinician programmer 50, and patient programmer 52 may communicate via cables or a wireless communication, as shown in FIG. 1. Clinician programmer 50 and patient programmer 52 may, for example, communicate via wireless communication with neurostimulator 32 using RF telemetry techniques known in the art. Clinician programmer 50 and patient programmer 52 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

However, clinician programmer 50 and patient programmer 52 need not communicate wirelessly. For example, in other embodiments, programmers 50 and 52 may communicate via a wired connection, such as via a serial communication cable, or via exchange of removable media, such as magnetic or optical disks, or memory cards or sticks. Further, the clinician programmer 50 may communicate with patient programmer 52 via remote telemetry techniques known in the art, communicating via a local area network (LAN), wide area network (WAN), public switched telephone network (PSTN), or cellular telephone network, for example.

Figure 4:
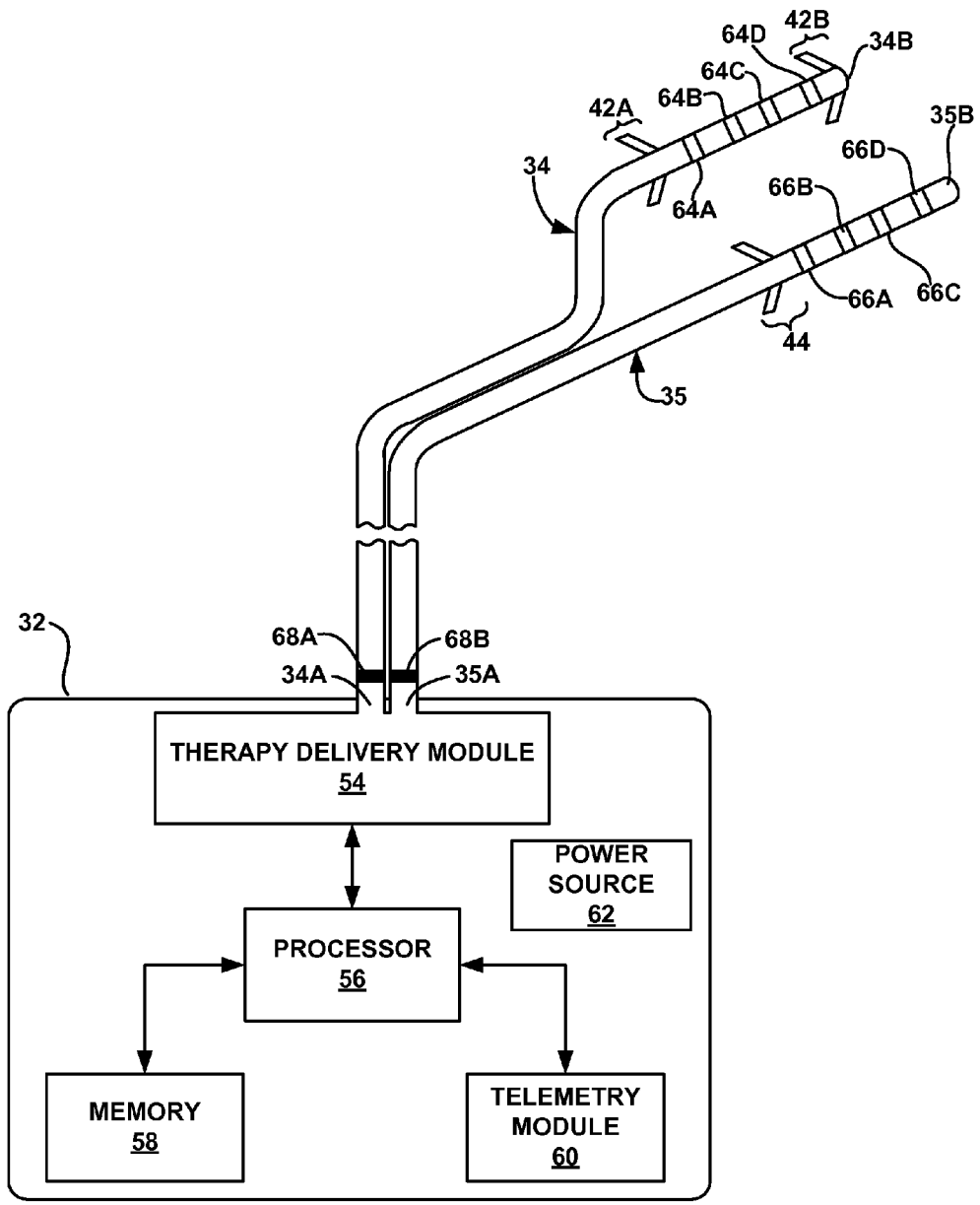
FIG. 4 is a schematic block diagram illustrating various components of an electrical stimulator and two implantable leads.

FIG. 4 is a block diagram illustrating various components of neurostimulator 32 and implantable leads 34 and 35 of therapy delivery system 30. Neurostimulator 32 includes therapy delivery module 54, processor 56, memory 58, telemetry module 60, and power source 62. In some embodiments, neurostimulator 32 may also include a sensing circuit (not shown in FIG. 4).

Electrodes 64A, 64B, 64C, and 64D (collectively "electrodes 64") are disposed on lead 34 adjacent to its distal end 34B. Electrodes 66A, 66B, 66C, and 66D (collectively "electrodes 66") are disposed on lead 35 adjacent its distal end 35B. The configuration, type, and number of electrodes 64 and 66 illustrated in FIG. 4 are merely exemplary. In some embodiments, electrodes 64 and 66 may be ring electrodes. In other embodiments, electrodes 64 and 66 may be segmented or partial ring electrodes, each of which extends along an arc less than 360 degrees (e.g., 90-120 degrees) around the periphery of leads 34 and 35, respectively.

In embodiments in which lead 34 is a paddle lead, electrodes 64 may extend along one side of lead 34. Electrodes 64 extending around a portion of the circumference of lead 34 or along one side of a paddle lead may be useful for providing an electrical stimulation field in a particular direction/targeting a particular therapy delivery site. For example, electrodes 64 may be disposed along lead 34 such that the electrodes face toward nerves within the occipital region 31 of patient 36, or otherwise away from the scalp of patient 36. This may be an efficient use of stimulation because electrical stimulation of the scalp may not provide any or may provide minimal useful therapy to patient 36. In addition, the use of segmented or partial ring electrodes 64 may also reduce the overall power delivered to electrodes 64 by neurostimulator 32 because of the efficient delivery of stimulation to the targeted nerve(s) by eliminating or minimizing the delivery of stimulation to unwanted or unnecessary regions within patient 36. Electrodes 66 of lead 35 may also extend along one side of lead 35 (if lead 35 includes a paddle-shaped portion) or may extend around a portion of lead 35, as described with respect to electrodes 64 of lead 34.

In embodiments in which electrodes 64 extend around a portion of the circumference of lead 34 or along one side of a paddle lead, lead 34 may include one or more orientation markers 68A proximate to proximal end 34A that indicate the relative location of electrodes 64. Orientation marker 68A may be a printed marker on lead 34, an indentation in lead 34, a radiographic marker, or another type of marker that is visible or otherwise detectable (e.g., detectable by a radiographic device) by a clinician. Orientation marker 68A may help a clinician properly orient lead 34 such that electrodes 64 face the desired direction (e.g., away from the scalp) when lead 34 is implanted within patient 36. For example, orientation marker 68A may also extend around the same portion of the circumference of lead 34 or along the side of the paddle lead as electrodes 64. In this way, orientation marker 68A faces the same direction as electrodes 64, thus indicating the orientation of electrodes 64 to the clinician. When the clinician implants lead 34 in the patient, orientation marker 68A may remain visible to the clinician. Lead 35 may also include one or more orientation markers 68B.

As FIG. 4 illustrates, leads 34 and 35 include fixation elements 42A-B and 44, respectively. In particular, lead 34 includes fixation elements 42A proximal to electrodes 64 and fixation elements 42B distal to electrodes 64. Fixation elements 42A and 42B may help locally fix electrodes proximate to target stimulation site 38 (FIG. 1). In other embodiments, lead 35 may also include fixation elements located both proximally and distally to electrodes 66, or alternatively, lead 35 may only include fixation elements distal to electrodes 66. In other embodiments, leads 34 and 35 may include fixation elements at any suitable location along the length of the respective lead bodies to fix leads 34 and 35 at various points between proximal ends 34A, 35A and distal ends 34B and 35B. The "length" is generally measured from the respective proximal end 34A, 35A to the respective distal end 34B, 35B of leads 34 and 35.

Neurostimulator 32 delivers stimulation therapy to target tissue sites 38 and 39 via electrodes 64 and 66, respectively, of leads 34 and 35. Electrodes 64 and 66 are electrically coupled to a therapy delivery module 54 of neurostimulator 32 via conductors within leads 34 and 35, respectively. More specifically, proximal end 34A of lead 34 includes contacts (not shown) to electrically couple electrodes 64 directly to connector 33 of neurostimulator 32 or indirectly to neurostimulator 32 (e.g., via a lead extension). Similarly, proximal end 35A of lead 35 includes contacts (not shown) to electrically couple electrodes 66 directly to connector 33 of neurostimulator 32 or indirectly to neurostimulator 32 (e.g., via a lead extension). In one embodiment, an implantable signal generator or other stimulation circuitry within therapy delivery module 54 delivers electrical signals (e.g., pulses or substantially continuous-time signals, such as sinusoidal signals) to targets stimulation sites 38 and 39 (FIG. 1) via at least some of electrodes 64 and 66 under the control of a processor 56. The implantable signal generator may be coupled to power source 62. Power source 62 may take the form of a small, rechargeable or non-rechargeable battery, or an inductive power interface that transcutaneously receives inductively coupled energy. In the case of a rechargeable battery, power source 62 similarly may include an inductive power interface for transcutaneous transfer of recharge power.

The stimulation energy generated by therapy delivery module 54 may be formulated as neurostimulation energy, e.g., for treatment of any of a variety of neurological disorders, or disorders influenced by patient neurological response. The signals may be delivered from therapy delivery module 54 to electrodes 64 and 66 via a switch matrix and conductors carried by leads 34 and 35 and electrically coupled to respective electrodes 64 and 66.

Processor 56 may include a microprocessor, a controller, a DSP, an ASIC, an FPGA, discrete logic circuitry, or the like. Processor 56 controls the implantable signal generator within therapy delivery module 54 to deliver neurostimulation therapy according to selected stimulation parameters. Specifically, processor 56 controls therapy delivery module 54 to deliver electrical signals with selected amplitudes, pulse widths (if applicable), and rates specified by the programs. In addition, processor 56 may also control therapy delivery module 54 to deliver the neurostimulation signals via selected subsets of electrodes 64 or 66 with selected polarities. For example, electrodes 64 may be combined in various bipolar or multi-polar combinations to deliver stimulation energy to selected sites, such as nerve sites adjacent an occipital nerve, spinal column, pelvic floor nerve sites, or cranial nerve sites. Electrodes 66 may also be combined in various bipolar or multi-polar combinations to deliver stimulation energy to selected sites, such as nerve sites adjacent the spinal column, pelvic floor nerve sites, or cranial nerve sites.

Processor 56 may also control therapy delivery module 54 to deliver each signal according to a different program, thereby interleaving programs to simultaneously treat different symptoms or provide a combined therapeutic effect. For example, in addition to treatment of one symptom such as migraine headaches, neurostimulator 32 may be configured to deliver neurostimulation therapy to treat other symptoms such as back pain. In such an embodiment, electrodes 64 of lead 34 may be positioned to deliver stimulation therapy for treating one symptom, and electrodes 66 of lead 35 may be positioned to deliver stimulation therapy for treatment of another symptom.

Memory 58 of neurostimulator 32 may include any volatile or non-volatile media, such as a RAM, ROM, NVRAM, EEPROM, flash memory, and the like. In some embodiments, memory 58 of neurostimulator 32 may store multiple sets of stimulation parameters that are available to be selected by patient 36 via patient programmer 52 (FIG. 1) or a clinician via clinician programmer 50 (FIG. 1) for delivery of neurostimulation therapy. For example, memory 58 may store stimulation parameters transmitted by clinician programmer 50 (FIG. 1). Memory 58 also stores program instructions that, when executed by processor 56, cause neurostimulator 32 to deliver neurostimulation therapy. Accordingly, computerreadable media storing instructions may be provided to cause processor 56 to provide functionality as described herein.

In particular, processor 56 controls telemetry module 60 to exchange information with an external programmer, such as clinician programmer 50 and/or patient programmer 52 (FIG. 1), by wireless telemetry. In addition, in some embodiments, telemetry module 60 supports wireless communication with one or more wireless sensors that sense physiological signals and transmit the signals to electrical stimulator 32.

Figure 5:
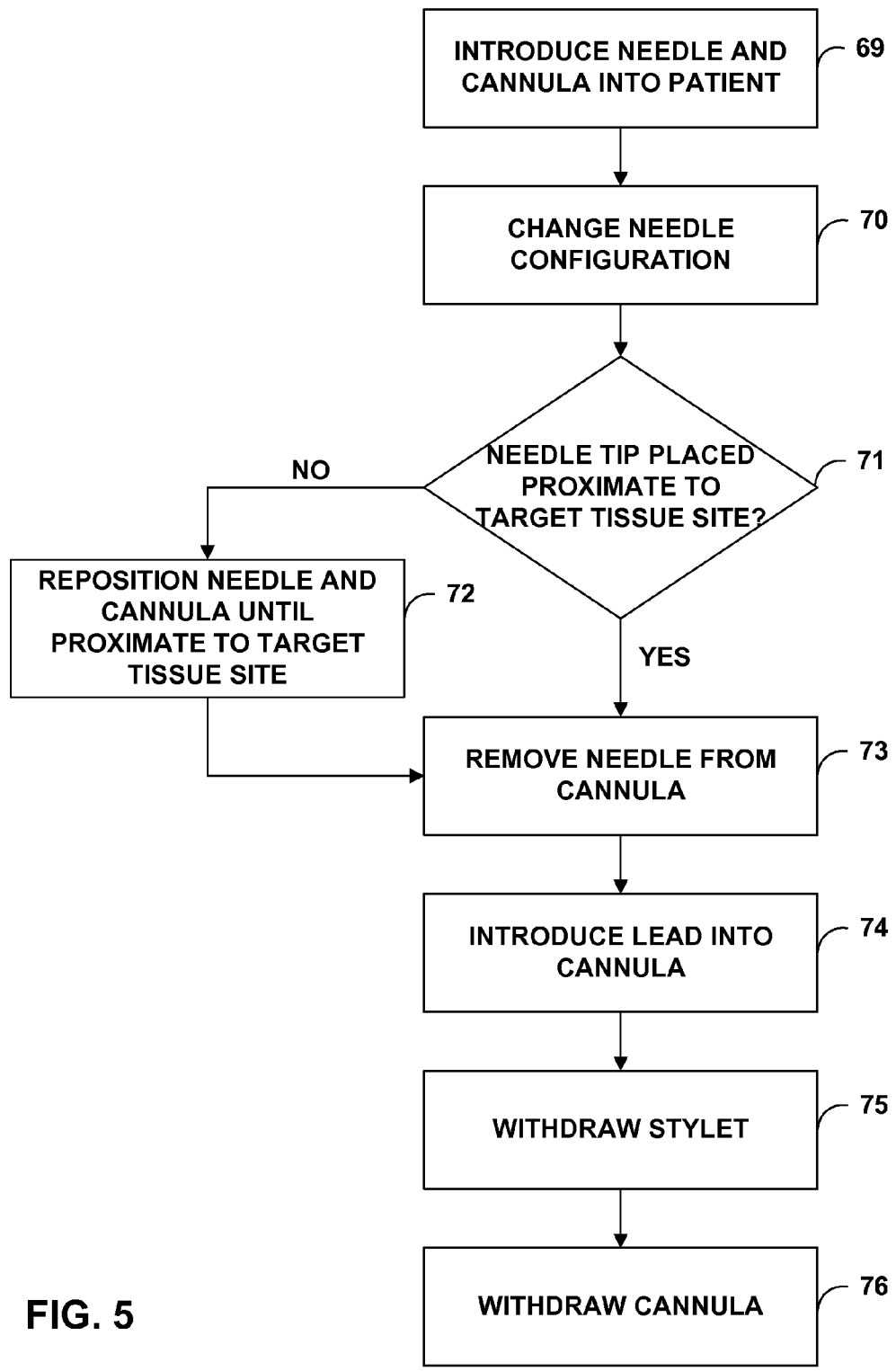
FIG. 5 is a flow diagram illustrating a technique for implanting a medical device proximate to an occipital nerve or a trigeminal nerve within an occipital region of a patient.

FIG. 5 is a flow diagram illustrating a technique for implanting an electrical lead proximate to an occipital region of patient 36 for stimulation, whether unilateral, bilateral or otherwise, of one or more occipital nerves or a trigeminal nerve. Implant tool 10 provides a clinician with a simple, effective, and easy to handle device for defining an insertion path for a medical device from an entry point in the patient's skin or scalp to a target tissue site within the occipital region 31. A clinician introduces needle 18 of implant tool 10 into patient 36, and cannula 24, which is disposed around needle 18, is tunneled through tissue by using a forward and upward motion following the curve of needle 18 (69). Distal tip 22 of needle 18 provides a sharp edge to tunnel through tissue. Examples of different entry points in which needle 18 may be introduced are described below with reference to FIGS. 6A-C and 7A-D.

The clinician may manually change the shape of malleable needle 18 to accommodate anatomical features (e.g., the curve of the patient's skull) and define an insertion path that follows a curve or bend that may be specific to a particular patient (70). The malleable needle 18 may allow a clinician to more accurately position needle 18 and cannula 24 within patient 36 by allowing the clinician to shape needle 18 as the need arises. The ability of needle 18 to change shape based on the specific patient or implant site may help reduce the likelihood of trauma to surrounding tissue, particularly with respect to an anatomical structure having an irregular shape or a shape that varies between patients, such as the back of the neck.

The clinician may shape needle 18 while needle 18 is disposed within patient 36, such as by providing the force necessary to bend or flex needle from an outer surface of the patient's skin or scalp. Alternatively, the clinician may partially or entirely withdraw needle 18 and, in some cases, cannula 24 from patient 36 to manipulate the shape of needle 18.

Upon introducing needle 18 and cannula 24 into patient 36, the clinician may determine whether distal point 22 of needle 18 is positioned proximate to the target tissue site within the occipital region 31 of patient 36 (71). For example, the clinician may deliver stimulation energy to electrode 20 or distal tip 22, and receive patient feedback in order to determine whether tip 22 of needle 18 is located proximate to target tissue site 38. If the placement of needle 18 is unsuccessful, the clinician may attempt to reposition needle 18 and cannula 24 (72). If the placement of needle 18 is successful, the clinician may continue to implant lead 34. After placement of needle 18 relative to target tissue site 38 is confirmed (71), needle 18 may be withdrawn from inner lumen 29 of cannula 24 (73) by withdrawing needle 18 while holding the portion of cannula 24 that remains outside of entry point 82 so that cannula 24 remains substantially in place. Cannula 24 is formed at least in part of a material that exhibits shape memory properties, and accordingly, upon withdrawal of needle 18 from cannula 24, cannula 24 changes from a first shape to a second shape. The heat from surrounding tissue may heat cannula 24, which may cause cannula 24 to transfigure from the first shape to the second shape. Alternatively, the removal of the "load" imposed by needle 18 on cannula 24 may activate the shape change or memory of a superelastic cannula 24.

Lead 34 (or lead 35), with or without the aid of a stylet disposed within a stylet lumen of lead 34, may then be introduced into inner lumen 29 of cannula 24 (74). A stylet may help provide rigidity to lead 34, which facilitates the handling of lead 34 as lead 34 is advanced through inner lumen 29 of cannula 24. The position of lead 34 relative to a distal end 24B of cannula 24, which typically indicates the relative location of target tissue site 38, may be confirmed with the aid of depth markers on lead 34 and/or with the aid of medical imaging techniques, such as fluoroscopy. Lead 34 and cannula 24 may include radio-opaque markers that are visible using imaging techniques, and the clinician may use the relative locations between the radio-opaque markers to determine the position of lead 34 relative to cannula 24. The stylet, if used, may then be removed from lead 34 (75) and cannula 24 may be removed from patient (76).

Prior to removing cannula 24 (76), the clinician may confirm the placement of electrodes 64 relative to target tissue site 38 by, for example, delivering electrical stimulation to electrodes 64 and receiving patient feedback. By leaving cannula 24 within the insertion path, the insertion path remains unobstructed until lead 34 is properly positioned within patient 36. This enables the clinician to readjust the position of lead 34 with ease, if necessary.

Figure 6A:
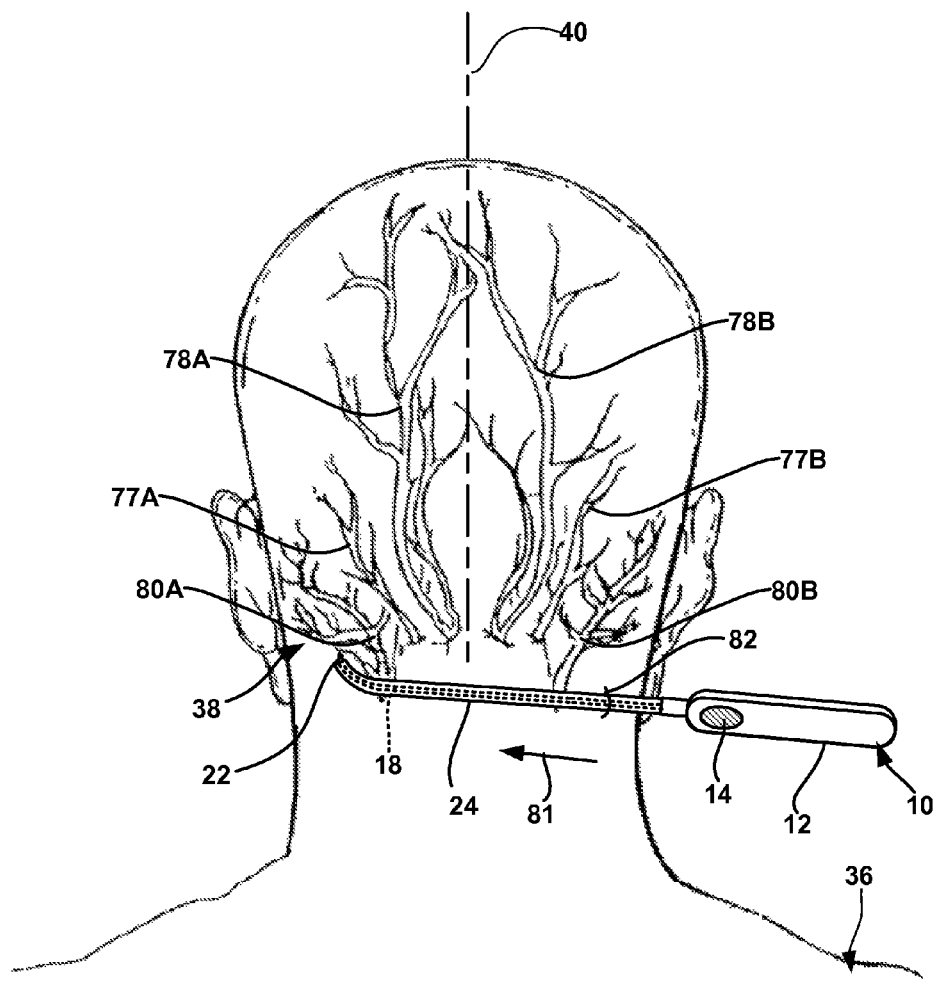
FIGS. 6A-6C illustrate various stages of a procedure for implanting a medical lead proximate to an occipital nerve with the aid of an implant tool including a needle and cannula.
Figure 6B:
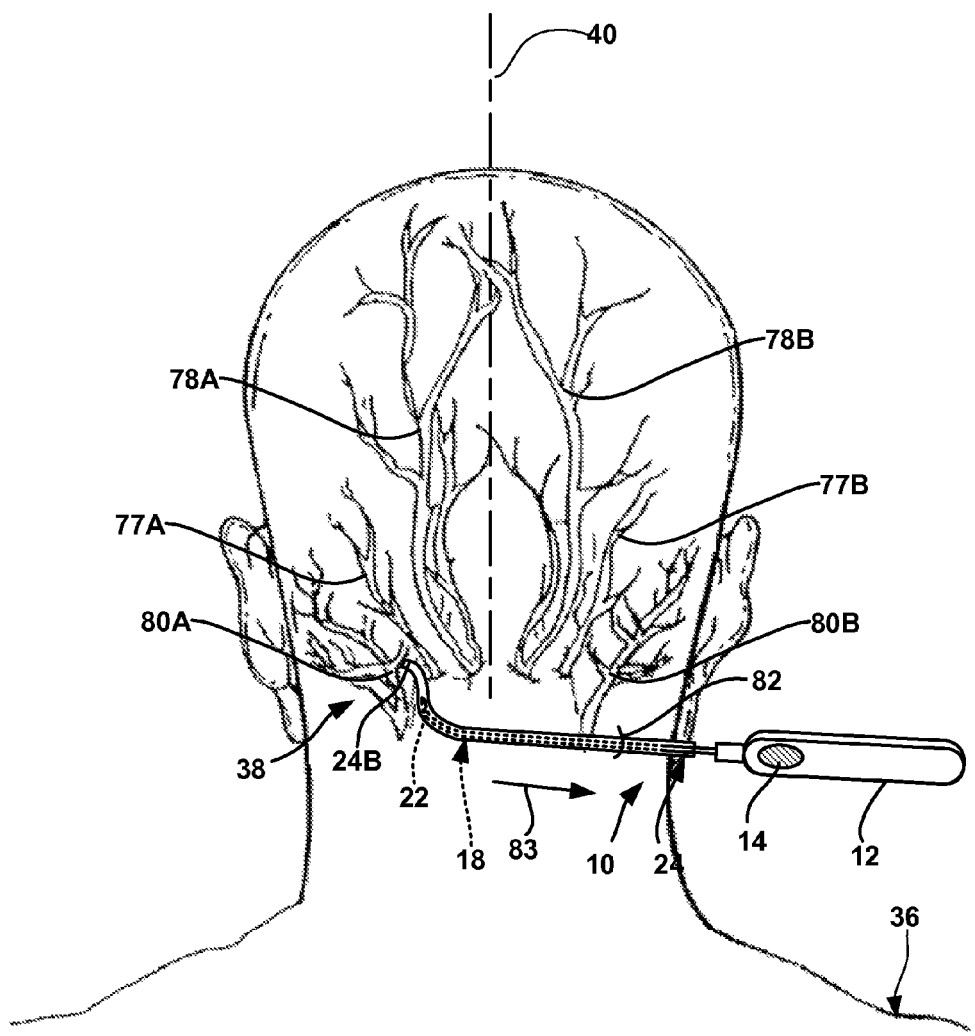
Figure 6C:
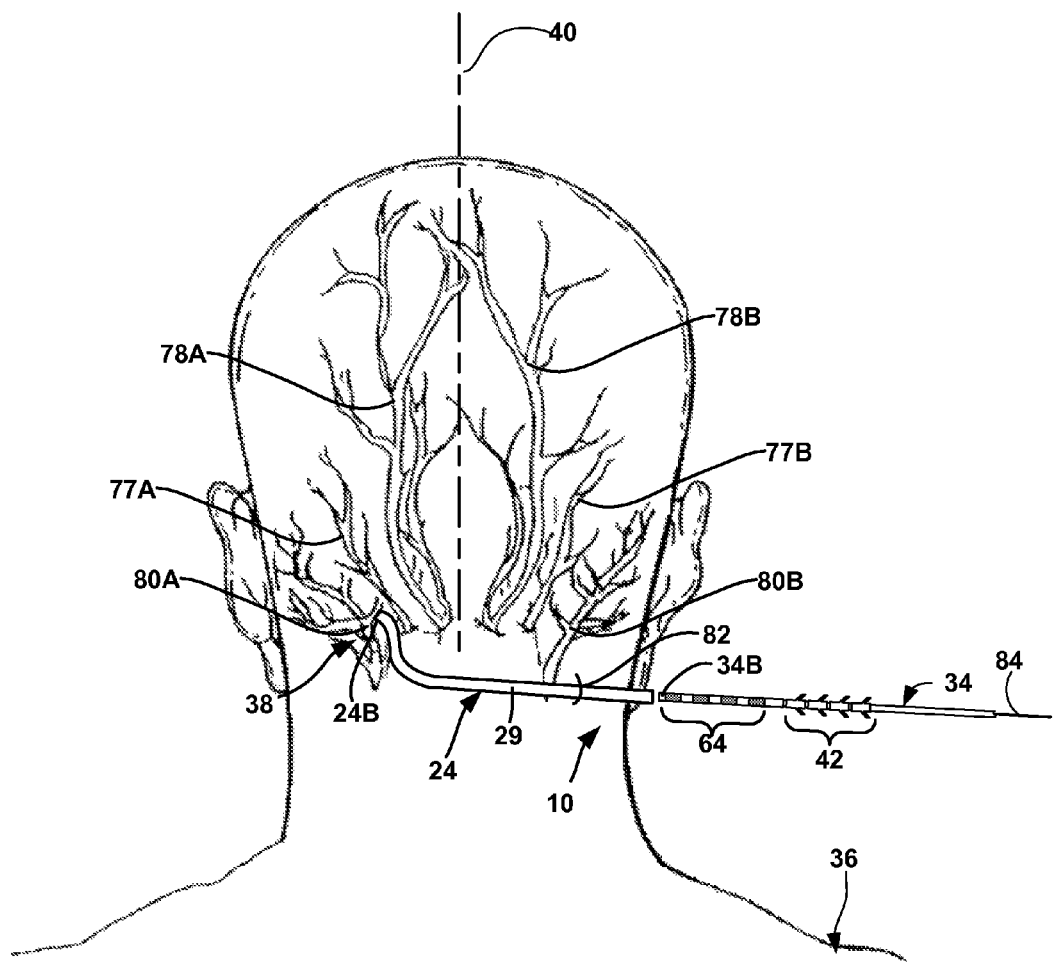

FIGS. 6A-6C and 7A-D illustrate the implantation of lead 34 within occipital region 31 of patient 16 with the aid of implant tool 10. FIGS. 6A-C illustrates a process for implanting lead 34 proximate occipital region 31 of patient 36 for stimulation of one or more occipital nerves, while FIG. 7A-D illustrates a process for implanting lead 34 proximate to occipital region 31 of patient 35 for stimulation of a trigeminal nerve. While FIGS. 6A-C and 7A-D are described with reference to lead 34, in other embodiments, another medical device, such as a catheter, microstimulator or otherwise, may be implanted in patient 36 using implant tool 10. Furthermore, the processes shown in FIGS. 6A-C and 7A-D may also be used to implant lead 35.

FIG. 6A illustrates the back of the head of patient 36, and shows branches of lesser occipital nerve 77A-B (collectively "occipital nerve 77"), greater occipital nerve 78A-B (collectively "occipital nerve 78"), and third occipital nerve 80A-B (collectively "occipital nerve 80"). Branches 77A, 78A, and 80A are on an opposite side of midline 40 from branches 77B, 78B, and 80B. Prior to beginning implantation of lead 34, a local anesthetic may be applied to anesthetize target tissue site 38, as well as areas of tissue that needle 18 will traverse to define an insertion path from entry point 82 to target tissue site 38. In general, tissue posterior to occipital region 31 may be anesthetized. Since embodiments of the technique for implanting a medical device within occipital region 31 permit the use of a local anesthetic, patient 36 may be treated on an out-patient basis, which may reduce costs over in-patient care and reduce recovery time. Also, by using local anesthesia, as opposed to general anesthesia, the implanting clinician may use conscious sensory responses to stimuli (such as trial stimulation pulses) from patient 36 to aid in placing implant tool 10 and stimulation lead 34. Using conscious sensory responses from patient 36 during placement of stimulation lead 34 may allow accurate placement of lead 34, may reduce the potential for an ineffective therapy, and reduce the potential for patient 36 injury caused by a misplaced lead. In other embodiments, other forms of anesthesia can be used, such as general anesthesia.

Once patient 36 has been anesthetized, implant tool 10 may be percutaneously introduced into patient 16 at entry point 82, as illustrated in FIGS. 6A-C, which may be created with a distal tip 22 of needle 18 of implant tool 10. Alternatively, a small incision may be made to define entry point 82. The incision may be approximately two centimeters in length is made in the neck of patient 36 lateral to the midline of the spine at the level of the C1 vertebra. Fluoroscopy or another medical imaging technique may be used to identify the C1 vertebra. The length of the skin incision may vary depending on the patient.

A clinician may grasp implant tool 10 with one hand, and introduce implant tool 10 into patient 36 through entry point 82. The direction in which implant tool 10 is introduced into patient 36 is indicated by arrow 81. The process of inserting and guiding implant tool 10 may involve the subcutaneous placement of needle 18 (and cannula 24, which is partially disposed around needle 18) across one or more occipital nerves 77, 78, and/or 80 that are causing patient 36 to experience pain. In the illustrated embodiment, implant tool 10 is introduced into the subcutaneous tissue, superficial to the fascia and muscle layer but below the skin. Occipital nerves 77, 78, and 80 are located within the cervical musculature and overlying fascia, and as a result, implant tool 10 is inserted superior to occipital nerves 77, 78, and 80. That is, in one embodiment, implant tool 10 is introduced into the fascia layer of patient 36 such that needle 18 and cannula 24 are between the skin of patient 36 and target tissue site 38 (FIG. 1). The approximate location of target tissue site 38 may be found using anatomical landmarks, fluoroscopy, or x-ray imaging. In order to locate the specific nerve causing pain, a clinician may palpate the area of pain.

Needle 18 defines an insertion path from entry point 82 to target tissue site 38, where the insertion path is substantially transverse to occipital nerves 77, 78, and 80. In the embodiment shown in FIGS. 6A-C, distal tip 22 of needle 18 is guided to target tissue site 38, which in the embodiment shown in FIGS. 6A-C is proximate to third occipital nerve 80A. In FIGS. 6A-7D, the portions of cannula 24 that are partially inserted into patient 36 are not shown in phantom for clarity of illustration. FIGS. 6A-7D, as well as the other figures, are not drawn to any particular scale.

Needle 18 and cannula 24, which substantially conforms to the shape of needle 18 when needle 18 is introduced in the inner lumen 29 of cannula 24, may be manipulated to conform to the back of the neck or other anatomical structure of patient 36. The clinician may advance needle 18 and cannula 24 toward target tissue site 38 in a series of steps by partially inserting needle 18 and cannula 24, withdrawing needle 18 and cannula to manually manipulate needle 18 into a desired shape, and re-insert needle 18 and cannula 24 into patient 36 to further advance tool 10 towards target tissue site 38. In this way, needle 18 is used to steer the direction of an insertion path through tissue for a medical device. The clinician may use fluoroscopic guidance or another suitable technique to identify occipital nerves 77, 78, and 80 and determine how to manipulate needle 18 to conform to the back of the neck of patient 36. In other words, the clinician may use fluoroscopy to aid in determining the length and angle of the portion of needle 18 to manipulate, as well as to aid in placement of needle 18 adjacent to a target tissue site 38.

Needle 18 and cannula 24 define implant tool 10 having a relatively small outer perimeter (e.g., a diameter) in order to provide a minimally invasive apparatus for defining an insertion path from entry point 82 at the skin of patient 36 to target tissue site 38. The relatively small diameter of needle 18 and cannula 24 help to minimize damage to tissue during the implantation process. When a clinician is implanting lead 34 within patient 36, the clinician may require more than one try to find an optimal target stimulation site 38. For example, the clinician may withdraw and reinsert implant tool 10 one or more times.

The clinician may confirm the position of implant tool 10 relative to target stimulation site 38 using imaging techniques, such as fluoroscopy. Alternatively, or additionally, implant tool 10 may be attached to or integrated with a test stimulator (not shown) that produces electrical stimulation to verify accurate placement of needle 18 relative to target stimulation site 18. For example, the test stimulator may include an electrical stimulation pulse generator electrically coupled to needle 18 via an electrical conductor and electrically coupled to a ground electrode pad, which may be attached to an exterior location of patient 36.

Needle 18 may include electrode 20 (FIGS. 1A-B) near tip 22 of needle 18 to deliver electrical pulses to surrounding tissue. Alternatively, needle 18 itself may be electrically conductive and may act as an electrode. In some embodiments, the majority of needle 18 is electrically insulated from electrode 20 so that stimulation energy can be generally confined to regions of needle 18 proximate to tip 22. Upon delivery of stimulation energy to electrode 20, the clinician may receive patient feedback in order to determine whether tip 22 of needle 18 is located proximate to target tissue site 38. The patient feedback may indicate, for example, whether the electrical stimulation is felt, whether the electrical stimulation induces paresthesia, whether patient 36 is afflicted by any side effects, and so forth. Alternatively, the clinician may confirm proper placement of implant tool 10 by relying on anatomical landmarks (e.g., the C1 vertebra).

Once needle 18 is appropriately positioned near the target tissue site 38, needle 18 is removed from cannula 24 so that cannula 24 remains positioned adjacent to target tissue site 38 to keep the insertion path from entry point 82 to target tissue site substantially free of any obstructions. FIG. 6B shows needle 18 partially withdrawn from cannula 24. The clinician may grasp handle 12 of implant tool 10 and withdraw handle 12, which is attached to needle 18, away from entry point 82, as indicated by arrow 83. The clinician may also hold cannula 24 in place in order to prevent cannula 24 from being withdrawn with needle 18. As needle 18 is withdrawn, cannula 24 remains at least partially within patient 36, while a portion of cannula 24 remains outside of patient 36. Cannula 24 has a length that is great enough to extend from target tissue site 38 within occipital region 31 of patient 36 to entry point 82, and in particular, past entry point 82.

When needle 18 is disposed within the inner lumen of cannula 24, cannula 24 substantially maintains the shape of needle 18 because needle 18 is more rigid than cannula 24 and thus, provides the dominant shape. Cannula 24, however, has a shape memory and upon the withdrawal of needle 18, cannula 24 assumes a shape other than that of needle 18. In the embodiment shown in FIG. 6B, distal end 24B of cannula 24 assumes curvilinear shape that is different than that of needle 18. In particular, distal end 24B of cannula 24 curves in a substantially opposite direction than that of distal tip 22B of needle 18.

FIG. 6C illustrates cannula 24 defining an insertion path for a medical device from entry point 82 to target stimulation site 38. The shape memory aspect of cannula 24 enables cannula 24 to define an insertion path through tissue that would not otherwise be possible with needle 18. Needle 18 may not be formed to have the same shape as cannula 24 for various reasons. For example, in some embodiments, needle 18 may not be able to achieve certain curvilinear shapes because it may be more rigid than cannula 24. As another example, it may be desirable for needle 18 to assume a particular shape (e.g., substantially straight with a curved distal end, as shown in FIGS. 1A-1B) in order to reach tissue near target tissue site 18. If needle 18 had the curvilinear shape of cannula 24 shown in FIG. 6C, it may be difficult for the clinician to direct needle at target tissue site 38 without causing undue damage to surrounding tissue. A needle 18 shape that has a substantially straight portion may be easier to guide through the tissue than a needle having the shape of cannula 24 shown in FIG. 6C.

In some embodiments, cannula 24 may assume another radius of curvature in order to define an insertion path that is better suited to reaching target stimulation site 38 proximate to occipital nerve 80, or any of the occipital nerves 77, 78 or a trigeminal nerve. For example, if it is desirable to implant lead 34 such that electrodes 64 are positioned around an outer perimeter of third occipital nerve 80, needle 18 may be shaped to reach occipital nerve 80, and cannula 24 may be shaped to partially wrap (or "hook") around at least part of the outer perimeter of occipital nerve 80 such that when lead 34 is introduced into inner lumen 29 of cannula 24, lead 34 also follows the path around at least a part of the outer perimeter of occipital nerve 80. Cannula 24 may also be moved slightly without needle 18 for fine adjustment of implant site. In some cases, cannula 24 may be slightly malleable so that the clinician may customize the shape of cannula 24 to target a desired tissue site 38.

In other embodiments, cannula 24 may assume another shape to help provide bias anchoring of tines 42 and facilitate controlled strain relief of the implanted lead 34. Due to the location of implanted lead 34 within the neck and/or back of patient 36, lead 34 may be subjected to pulling and stretching from muscle movement and the movement of the patient's neck and/or back, which may increase the chances of lead migration. By implanting lead 34 such that lead follows the curvilinear path of cannula 24, lead 34 may be implanted with extra slack to allows lead 34 to withstand some degree of pulling without causing electrodes 64 to become displaced relative to target tissue site 38 or without dislodging tines 42 when patient 36 moves. Extra slack may also be provided through other techniques, such as strain relief loops. In addition, tines 42 or another fixation mechanism on lead 34 may also help lead 34 substantially remain in place. The curvilinear path imparted by cannula 24 may define, for example, a sigmoid shape.

Depending on the particular patient 36, when target therapy delivery site 38 is located in the neck of patient 36 and electrical stimulator 32 is located in the back or chest cavity of patient 36, approximately up to four inches of slack may be necessary throughout the length of lead 34 (measured from proximal end 34A to distal end 34B) to prevent lead 34 from being pulled taut between target tissue site 38 and the implant site for electrical stimulator 32 during a range of movement of patient 36. The total amount of slack included throughout the length of lead 34 may be adjusted based on the relative locations of target tissue site 38 and electrical stimulator 32, as well as the size of patient 36. For example, when target therapy delivery site 38 is located in the head of patient 36 and electrical stimulator 32 is located in the buttock of patient 36, more slack is necessary than when electrical stimulator 32 is located in the abdomen of patient 36. This is at least partially attributable to the fact that when lead 34 traverses the hip region, lead 34 undergoes a greater range of movement, thereby increasing the amount of slack required to help prevent lead 36 from being pulled tight and dislodging fixation elements 42.

Implant tool 10 does not contain lead 34 when introduced into patient 36. However, inner lumen 29 of cannula 24 is sized to receive lead 34. As shown in FIG. 6C, lead 34 may be introduced into cannula 24 after needle 18 is withdrawn from cannula 34. Cannula 24 helps prevent the insertion path previously defined by needle 18 from becoming obstructed after needle 18 is removed from patient 36. Cannula 24 also serves as a lead introducer to guide lead 34 to target tissue site 38 within occipital region 31. In addition, cannula 24 may also help prevent premature engagement of fixation elements 42A-B with surrounding tissue by separating fixation elements 42A-B from surrounding tissue until lead 34 is properly positioned proximate to target tissue site 38.

In the embodiment of cannula 24 shown in FIG. 2B, cannula 24 has luer lock hub 25, which a clinician may use to connect to a fluid introduction device, such as a syringe, and/or may use to handle cannula 24. If cannula 24 has a handle similar to luer lock hub 25, handle 12 or otherwise, the handle of cannula 24 may include a inner lumen that is sized to receive lead 34 and is substantially aligned with inner lumen 29 of cannula 24. The clinician may then implant lead 34 through the handle of cannula 24 and into inner lumen 29 of cannula 24 to reach target tissue site 38.

Stylet 84 may be introduced into a stylet lumen within lead in order to help guide lead 34 through cannula 24 and to target stimulation site 38. Stylet 84 is more rigid than lead 34, which allows the clinician to more easily handle lead 34 as lead 34 is guided through cannula 24. Once lead 34 is in place such that electrodes 64 are located within operative distance of target tissue site 38 (i.e., a distance to provide sufficient stimulation to target tissue site 38), the stylet used to guide lead 34 and cannula 24 are removed from patient 36, typically through insertion point 82, and lead 34 is left in place to provide electrical stimulation to the target tissue site. As described above, lead 34 is substantially secured in place with tines 42. Tines 42 may be positioned such that as cannula 24 is removed from patient 36, tines 42 are deployed such that lead 34 remains in the curved path defined by cannula 24.

After distal end 34B of lead 34 is placed near occipital nerve 80, proximal end 34A (shown in FIG. 3) may be tunneled through tissue of patient 36 to electrical stimulator 32, which may be a trial or chronic stimulator. If electrical stimulator 32 is a chronic stimulator, the direction and location of tunneling, which may be, for example, through the neck, back or chest, typically depends on the implant location of electrical stimulator 32. Lead 34 may exit the patient's skin when attached to an external trial stimulator to evaluate stimulation therapy. In some embodiments, a percutaneous lead extension couples the lead to the external trial stimulator. In this manner, the lead may be used with an implantable electrical neurostimulator 32 if desired or an external trial stimulator. Following implantation of lead 34 or prior to implantation of lead 34, lead 35 may be implanted proximate to a branch of third occipital nerve 80B on an opposite side of midline 40 from third occipital nerve 80A, or alternatively, one or more other occipital nerves 77 or 78.

Implantation of two (or more) leads 34, 35 may be useful for stimulating more than one target stimulation site, for presenting a greater number of possible electrode configurations or for achieving bilateral stimulation. Electrical stimulation may be delivered by electrodes on one lead 34 or 35, or, alternatively, a combination of electrodes on both leads 34 and 35. As previously described, bilateral stimulation includes stimulation of two regions of patient 36 either sequentially or simultaneously. The two regions are typically on opposite sides of midline 40 (FIG. 1) of patient 16, and typically include two branches of a nerve. Bilateral stimulation may also be achieved with a single lead 34, where electrodes of the lead are positioned to span both regions of stimulation. For example, bilateral stimulation of an occipital nerve may be achieved by utilizing a single lead 34 that is placed such that electrodes 64 span both sides of the midline 40 of patient 36 and proximate to the branches of the one or more occipital nerves 77, 78, and/or 80 to be stimulated.

Figure 6D:
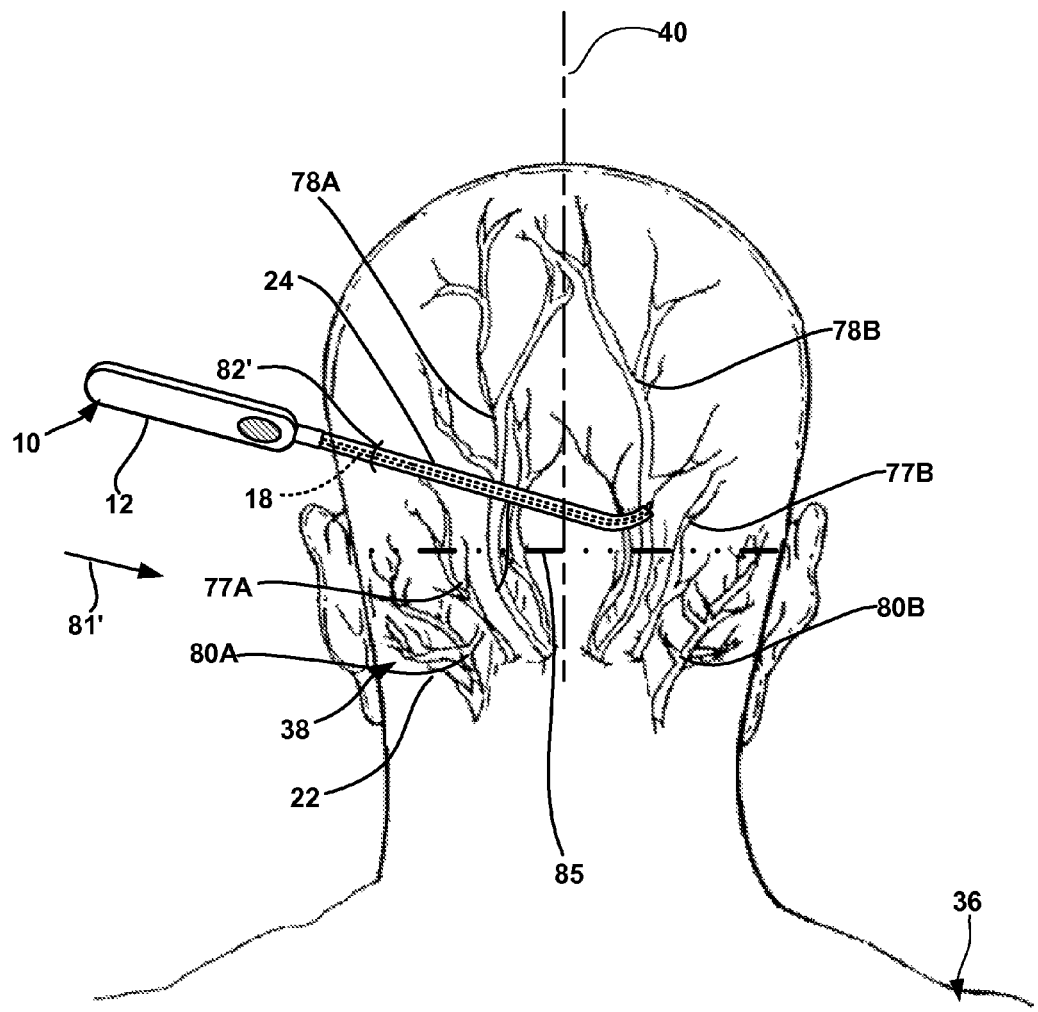
FIG. 6D illustrates another embodiment of a procedure for implanting a medical lead proximate to an occipital nerve with the aid of an implant tool including a needle and cannula.

FIG. 6D illustrates another embodiment of a technique that includes implanting lead 34 proximate to an occipital nerve 77, 78 or 80 with implant tool 10. The technique shown in FIG. 6D is similar to that shown in FIG. 6A, but entry point 82' is on an opposite side of a midline 40 of patient 36 from entry point 82 (FIG. 6A) and further from the patient's ear. Entry point 82' is selected to aid in placement of lead 34 at least partially along line 85.

As FIG. 6D illustrates, implant tool 10 may be percutaneously introduced through entry point 82', which may be created with a distal tip 22 of needle 18 of implant tool 10. Alternatively, a small incision may be made to define entry point 82. The clinician may grasp implant tool 10 with one hand, and introduce implant tool 10 into patient 36 through entry point 82 in a direction indicated by arrow 81'. The process of inserting and guiding implant tool 10 may be substantially similar to the one described above with respect to FIG. 6A. The clinician may curve needle 18 to substantially conform to the back of the patient's head in order to reduce trauma during the implantation procedure. Needle 18 and cannula 24 may be guided to a lead implantation site along line 85. For example, one or more sets of electrodes may be positioned along line 85 proximate to occipital nerves 77A and 77B for bilateral stimulation.

Figure 7A:
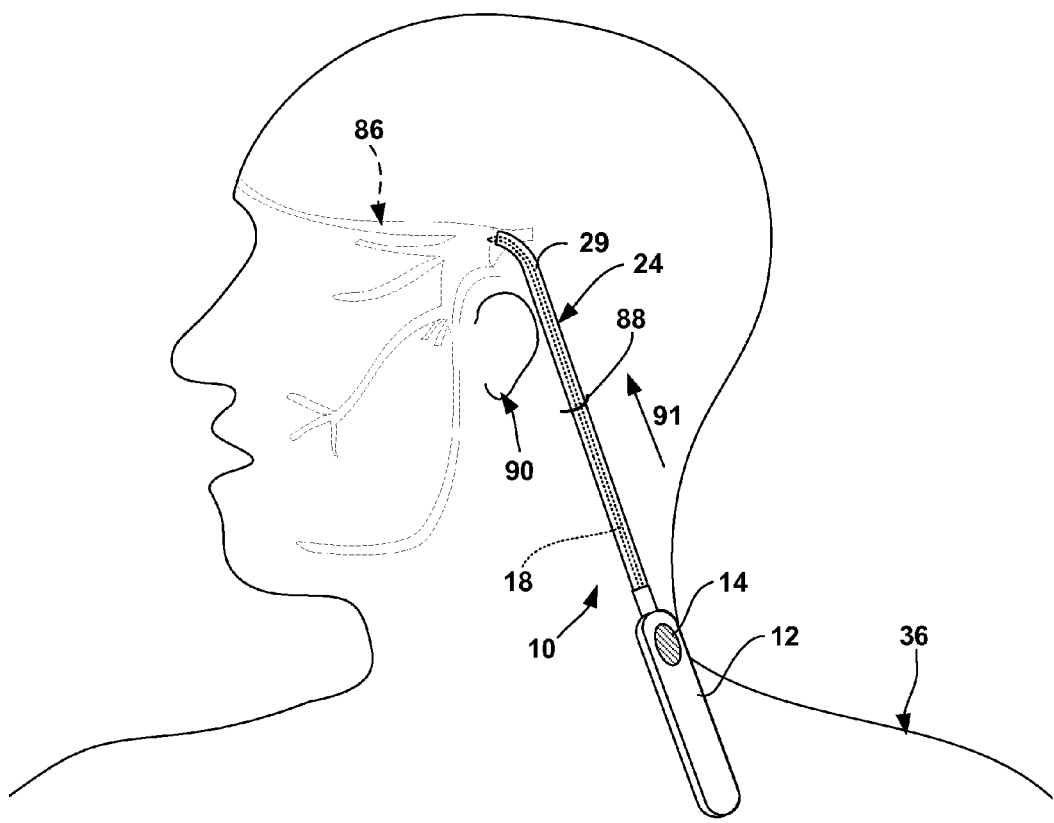
FIGS. 7A-7D illustrate various stages of a procedure for implanting a medical lead proximate to a trigeminal nerve with the aid of an implant tool including a needle and cannula.

Implant tool 10 may also be used to tunnel leads 34, 35 from target tissue sites 38, 39, respectively, to the implant site of electrical stimulator 32 (shown in FIG. 3). In addition, implant tool 10 may be used to access other nerves within occipital region 31 of patient 36. FIG. 7A illustrates an embodiment in which implant tool 10 is used to implant lead 34 proximate to a branch of trigeminal nerve 86 (shown in phantom lines). Trigeminal nerve 86, which is also known as the fifth cranial nerve, is responsible for sensation in the face as well as certain motor functions, such as biting, chewing, and swallowing. Stimulation of trigeminal nerve may help treat chronic headaches.

A clinician may find it desirable to introduce lead 34 into patient 36 through entry point 88, which may be located at or near the back of the patient's head. The location of entry point 88 may be selected to support the direction lead 34 is tunneled to an implant site for electrical stimulator 32 (FIG. 3). Another consideration when selecting the location of entry point 88 may be the appearance of patient 36. When entry point 88 is located behind the patient's ear 90 or otherwise near the back of the patient's head or near the patient's hairline, the clinician may not need to shave the patient's head and scars or other evidence of the entry point may be hidden from direct view. In one embodiment, entry point 88 is within approximately five inches (12.7 centimeters) of the patient's ear 90.

In order to reach some branches of trigeminal nerve 86, lead 34 may need to be routed around anatomical obstructions, such as the ear 90 and associated physiology. In addition, the insertion path from entry point 88 to trigeminal nerve 86 may be difficult to maneuver with a rigid implant tool. Implant tool 10 having a malleable needle 18 and shape memory cannula 24 may be useful for defining an insertion path for lead 34 around the anatomical obstructions.

In the embodiment of the technique for implanting lead 34 proximate to trigeminal nerve 86 shown in FIG. 7A, needle 18 and cannula 24 are guided up toward the portion of trigeminal nerve 86 that is above the patient's ear 90. As FIG. 7A illustrates, implant tool 10 may be introduced into patient 36 through entry point 88, which may be at any suitable location. Needle 18 and cannula 24 may be introduced into a layer of tissue that is superior to trigeminal nerve 86. Accordingly, unintentional damage or irritation to trigeminal nerve 86 during the tunneling of needle 38 is minimized. As with entry point 82 of FIGS. 6A-C, entry point 88 may be an incision or may be created by a sharp tip 22 of needle 18 of implant tool 10. The clinician may guide needle 18 and cannula 24 through tissue of patient 36 in an upward direction toward ear 90, as indicated by arrow 91. The curve near the distal tip 22 of needle 18 may help route the insertion path for lead 34 around ear 90. In FIG. 7A, those portions of needle 18 disposed within the inner lumen of cannula 24 are shown in phantom.

Figure 7B:
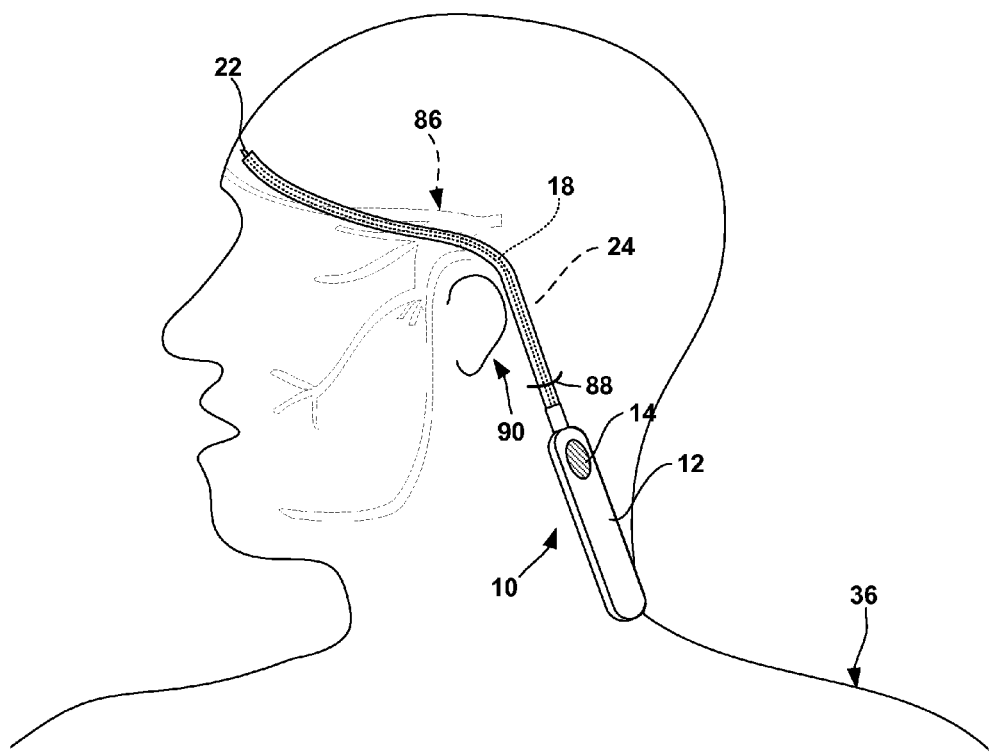

FIG. 7B illustrates needle 18 defining an insertion path that traverses around the ear 90 of patient 36. Cannula 24, which generally conforms to the shape of needle 18 when needle 18 is disposed within cannula 24, also traverses the insertion path around ear 90. As the clinician advances needle 18 into patient 36, the clinician may manually shape malleable needle 18 as necessary in order to achieve the configuration necessary for needle 18 and cannula 24 to traverse around ear 90 as well as to conform to the curve of the patient's head. The path around the patient's ear 90 and the curve of the patient's head are two anatomical features/structures that may differ between patients. Unlike implant tools that have a predefined shape that may not suit a particular patient, malleable needle 18 of implant tool provides the advantage of enabling the clinician to personalize the shape of implant tool 10 to the patient.

Figure 7C:
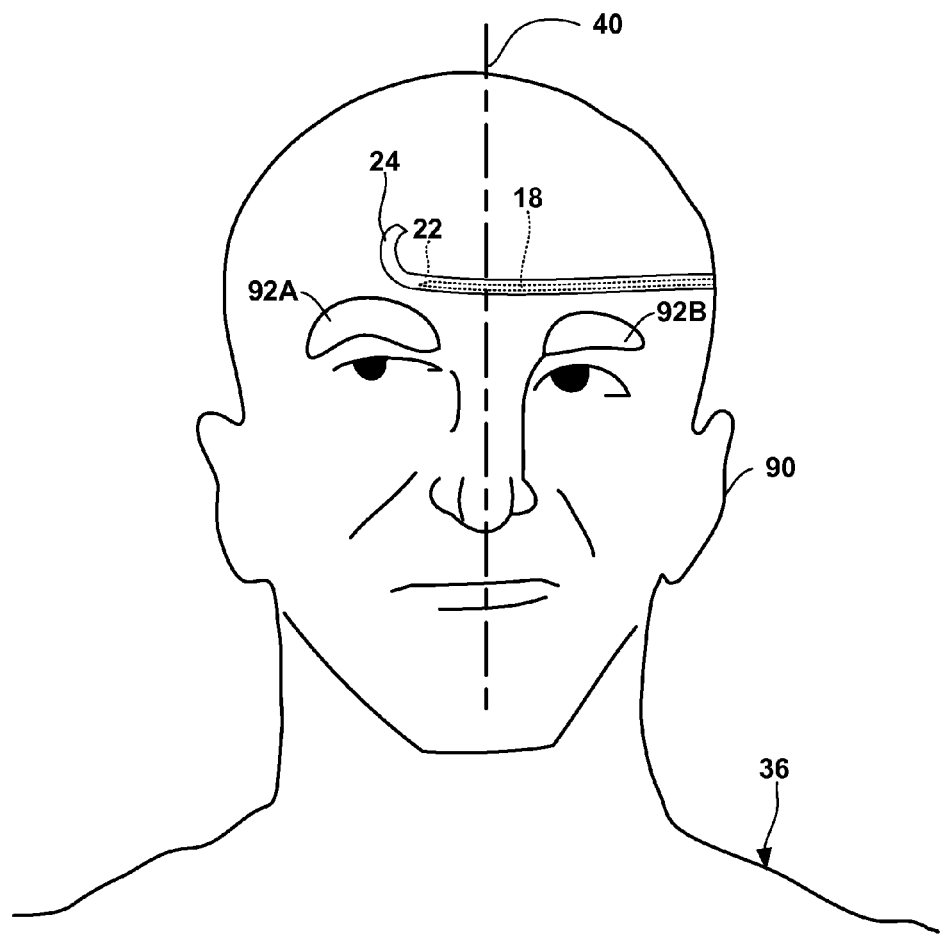

FIG. 7C illustrates a front view of patient 36, and illustrates needle 18 and cannula 24 defining an insertion path that traverses from behind ear 90 to a region superior to branches of trigeminal nerve 86 that are along the brow line of patient 36, and in particular, near eyebrows 92A-B. The clinician may grasp handle 12 of implant tool 10 and guide needle 18 and cannula 24 into patient 36 such that eventually, needle 18 and cannula 24 extend transversely across a brow line of patient 36. As previously described, the clinician may manually import a curve into needle 18 in order to define an implant tool 10 that follows the contour of the patient's head. Curving needle 18 as needle 18 and cannula 24 are introduced into patient 18 may help minimize the possibility of distal end 22 of needle 18 extending through the scalp or epidermis of patient 36.

Upon reaching the target tissue site proximate to trigeminal nerve 86, which the clinician may locate by delivering test stimulation via electrode 20 or distal tip 22 of needle 18, the clinician may withdraw needle 18 from cannula 24. In FIG. 7C, needle 18 has been partially withdrawn from cannula 24. Cannula 24 remains partially within patient 36 after needle 18 is withdrawn. As previously described, shape memory cannula 24 changes from a first shape to a second shape upon withdrawal of needle 18 from patient 16. In the embodiment shown in FIG. 7C, distal end 24B of cannula 24 curves away from eyebrows 92A-B.

Figure 7D:
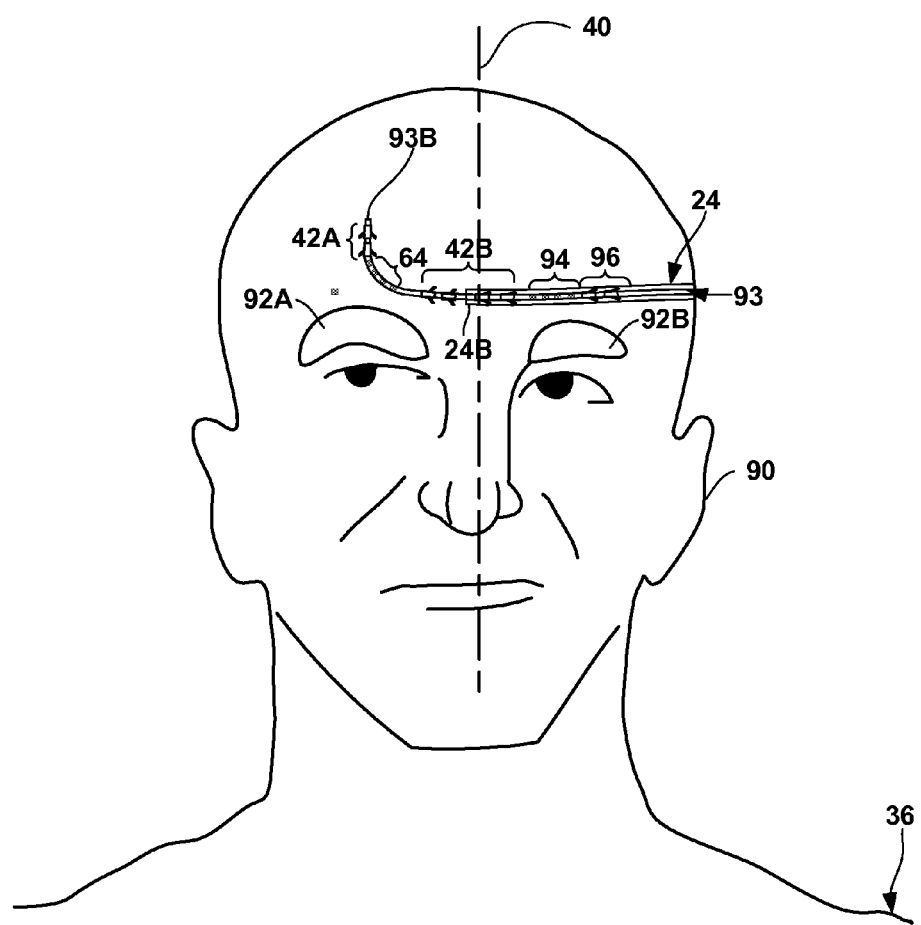

As FIG. 7D illustrates, after needle 18 is withdrawn from patient 36, cannula 24 further defines the insertion path for lead 93. By imparting some curvature to the insertion path, lead 93 may be implanted with extra slack, which provides strain relief to lead 93 upon implantation in patient 36. In addition, cannula 24 may help bias fixation elements 42 in a direction that helps lead 93 further resist pulling forces. In FIG. 7D, lead 93 is introduced into inner lumen 29 of cannula 24 and guided to the target tissue site proximate to trigeminal nerve 86 and near eyebrows 92A-B. Lead 93 is similar to lead 34 of FIG. 4, but includes two sets of electrodes 64, 94, where fixation elements 42A are distal to electrodes 64, fixation elements 42B are proximal to electrodes 64 and distal to electrodes 94, and fixation elements 96 are proximal to electrodes 94.

In order to achieve bilateral stimulation of trigeminal nerve 86 (FIGS. 6A-B), lead 93 may be implanted such that one set of electrodes 64 is implanted proximate to one branch of trigeminal nerve 86 on the same side of midline 40 (shown in FIG. 7C) as eyebrow 92A and another set of electrodes 94 is implanted proximate to a branch of trigeminal nerve 86 near eyebrow 92B on an opposite side of midline 40. For some patients, stimulation of trigeminal nerve 86 near eyebrows 92A-B may provide effective therapeutic results. In another embodiment, two different leads may be implanted proximate to a respective eyebrow 92A or 92B, rather than a single lead 93 that extends across midline 40 to stimulate two branches of trigeminal nerve 86.

Lead 93 may be advanced through cannula 24 until distal end 93B of lead 93 is deployed from cannula 24 or until distal end 93B of lead 93 is substantially aligned with a distal end 24B of cannula 24. The position of lead 93 relative to cannula 24 may be determined with the aid of medical imaging techniques, depth markers on lead 93 or any other suitable means. Cannula 24 may be withdrawn from patient 36, and as cannula 24 is withdrawn, fixation elements 42 and 96 are deployed into tissue and engage with surrounding tissue to substantially fix a position of lead 93 proximate to branches of trigeminal nerve 86 near eyebrows 92A-B. As cannula 24 is withdrawn from patient 36, fixation elements 42A, 42B, and 96 are sequentially deployed into tissue, thereby fixing lead 93 such that lead 93 has substantially the same curvature defined by cannula 24.

In other embodiments, it may be desirable to implant lead 93 to partially wrap around trigeminal nerve 86 such that electrodes 64 and/or 94 act as a "cuff" electrode. In those embodiments, cannula 24 may change from a first shape (e.g., a shape substantially similar to needle 18) to a second shape in which cannula 24 is configured to at least partially wrap around at least a part of the outer perimeter of trigeminal nerve 86. Therefore, when lead 93 is deployed into tissue through cannula 24, lead 93 also follows the path around at least a part of the outer perimeter of trigeminal nerve 86.

Figure 8:
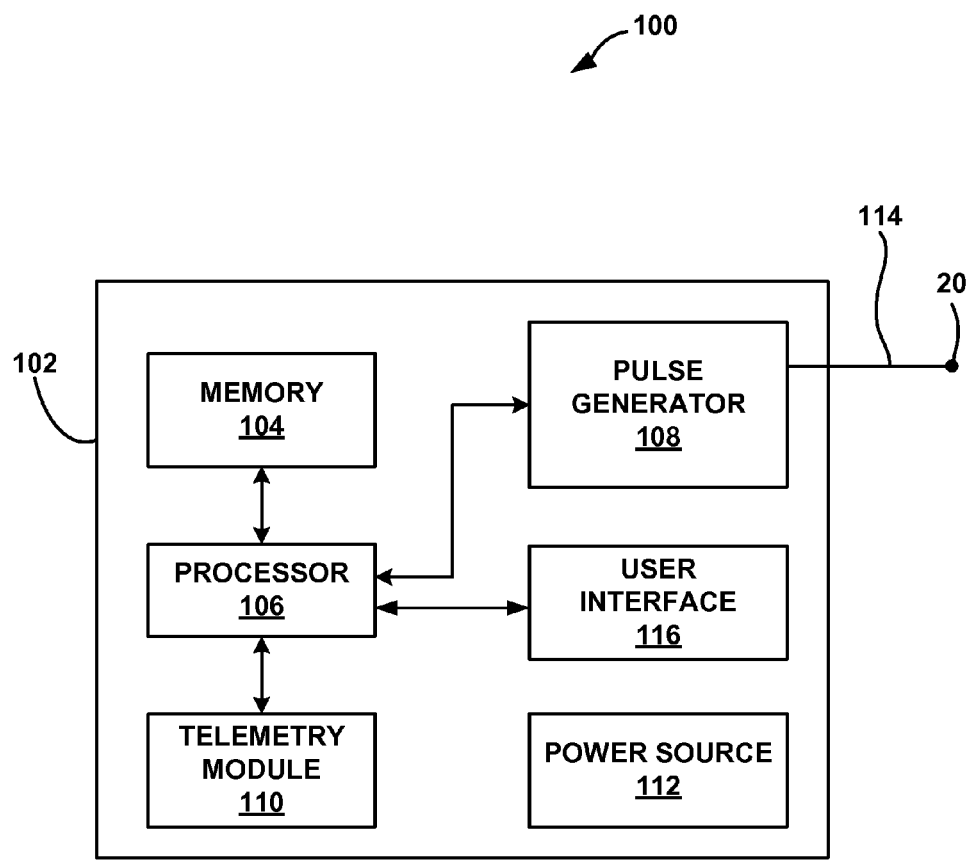
FIG. 8 is a functional block diagram illustrating various components of an implant tool capable of providing test stimulation.

FIG. 8 is a schematic diagram illustrating exemplary implant tool 100 capable of providing test stimulation for determining correct lead placement. Implant tool 100 is similar to implant tool 10 of FIG. 1A, but includes handle 102 that houses the electronics and a power source necessary to provide test stimulation pulses when determining the correct placement of needle 18 (shown in FIG. 1A). In particular, housing 102 includes memory 104, processor 106, pulse generator 108, telemetry module 110, power source 112, and user interface 116.

Memory 104 stores instructions for execution by processor 106, stimulation parameters and, optionally, information related to the use of needle 18. Memory 104 may include separate memories for storing instructions, stimulation parameter sets, and stimulation information, or a common memory. Pulse generator 108 is programmed with stimulation pulse parameters appropriate for delivery of test stimulation in the form of stimulation pulses delivered continuously or in selected bursts. Pulse generator 108 may be substantially similar to a trial or chronic stimulator used to treat the patient. The clinician may set test parameters for pulse generator 108 to reproduce.

Processor 106 controls pulse generator 108 to deliver electrical stimulation therapy. Based on stimulation parameters programmed by the clinician via user interface 116, processor 106 instructs appropriate stimulation by pulse generator 108. Information may also be received from user interface 116 at any time during operation, in which case a change in stimulation parameters may immediately occur. User interface 116 may be accessed directly on handle 102 as a set of switches, dials, buttons, or other input media, or accessed via an external programmer that transmits information to tool 100 by wired or wireless telemetry. User interface 116 also may include an LED or LCD display indicating the values of current stimulation parameters, battery life, and any operational information. Alternatively, user interface 116 may be a touch screen for modification of stimulation parameters. User interface 116 may be disabled by the clinician during test stimulation to eliminate the chance of unsafe stimulation modifications during handling of handle 102.

In some embodiments, wireless telemetry in implant tool 100 may be accomplished by radio frequency (RF) communication or proximal inductive interaction of implant tool 100 with another programming device via a telemetry interface (not shown). Processor 106 may control the telemetry interface to exchange information with the programming device. Processor 106 may transmit operational information and other information to the programming device via the telemetry interface. Processor 106 determines any pulse parameter adjustments based on the received information, and loads the adjustments into memory 104 for use during delivery of stimulation.

Power source 112 delivers operating power to the components of implant tool 100. Power source 112 may include a battery and a power generation circuit to produce the operating power. In some embodiments, the battery may be rechargeable to allow extended operation. Recharging may be accomplished through proximal inductive interaction between an external charger and an inductive charging coil within power source 112. In other embodiments, power source 112 may recharge though an alternating current adapter charger. Alternatively, power source 112 may directly utilize external power from an alternating current source, e.g., with appropriate isolation and ground fault interruption circuitry.

Once needle 18 is placed within occipital region 31, implant tool 100 may provide preliminary test stimulation pulses to specifically locate the best location to place a lead without the need to implant a lead or couple needle 18 to an additional device. The test stimulation pulses may be delivered via a dedicated electrode 20 (shown in FIG. 1A) at or near the distal tip 22 of needle 18. Alternatively, the entire needle 18 may be electrically conductive but insulated to isolate stimulation to a region at or near the distal tip 22. A ground electrode may placed on an external surface of patient 36 to provide for unipolar stimulation that is delivered by electrode 20 carried by needle 18. An appropriate location for placement of the ground electrode may be the neck, chest or back of patient 36.

Electrode 20 is electrically coupled to pulse generator 108 within handle 102 by conductor 114. Handle 100 may include a switch (not shown) to turn power source 112 on or off. When the clinician desires to analyze the location of the distal tip 22 of needle 18 for proximity to target tissue site 38, the switch may be slid to a first position to deliver test stimulation pulses and slide to a second position once test stimulation is no longer needed.

Implant tool 100 may be programmed through user interface 116. Parameters such as voltage amplitude, current amplitude, pulse width, pulse frequency, duty cycle or other stimulation parameters may be adjusted before or during test stimulation. Alternatively, the parameters of the stimulation energy output from implant tool 100 may be fixed, or include a series of pulses with different parameters according to a predetermined sequence. In other embodiments, parameters may be adjusted by connecting a programmer to handle 102 through a wired connection or wireless telemetry via telemetry module 110.

As a further alternative, handle 102 may simply provide an electrical terminal for connection to an external test stimulator, and thereby serve as an electrical conduit between the test stimulator and needle 18. In addition, implant tool 102 may be able to store stimulation information and transfer the information to another device via wired or wireless telemetry via telemetry module 110. In particular, implant tool 100 may include the capability to store stimulation information to memory to aid a clinician in efficiently providing test stimulation.

In some embodiments, implant tool 100 may be capable of delivering bipolar test stimulation. Needle 18 may include more than one electrode 20 to enable anode and cathode configurations for delivery of bipolar stimulation at or near the distal tip 22 of needle 18. In this case, the ground electrode attached to an exterior surface of patient 36 may not be necessary. Bipolar stimulation may provide more accurate test stimulation of occipital nerves 77, 78, 80 or trigeminal nerve 86.

Advantages of implant tool 100, in embodiments in which a stimulator is integrated with the tool, include fewer devices for the clinician to operate and shorter implantation time of a medical device. In some embodiments, implant tool 100 may include a channel though handle 102 and needle 18 to facilitate lead insertion directly though implant tool 100.

An implant tool 10, 100 including a malleable needle and shape memory cannula may also be used to implant medical devices other than medical leads. For example, implant tools 10, 100 may also be used to implant a fluid delivery conduit, such as a catheter, proximate to target tissue site 38. In some cases, the therapy regiment for patient 36 may require delivery of a drug to target tissue site 38 within occipital region 31 instead of or in addition to the delivery of electrical stimulation.

Figure 9:
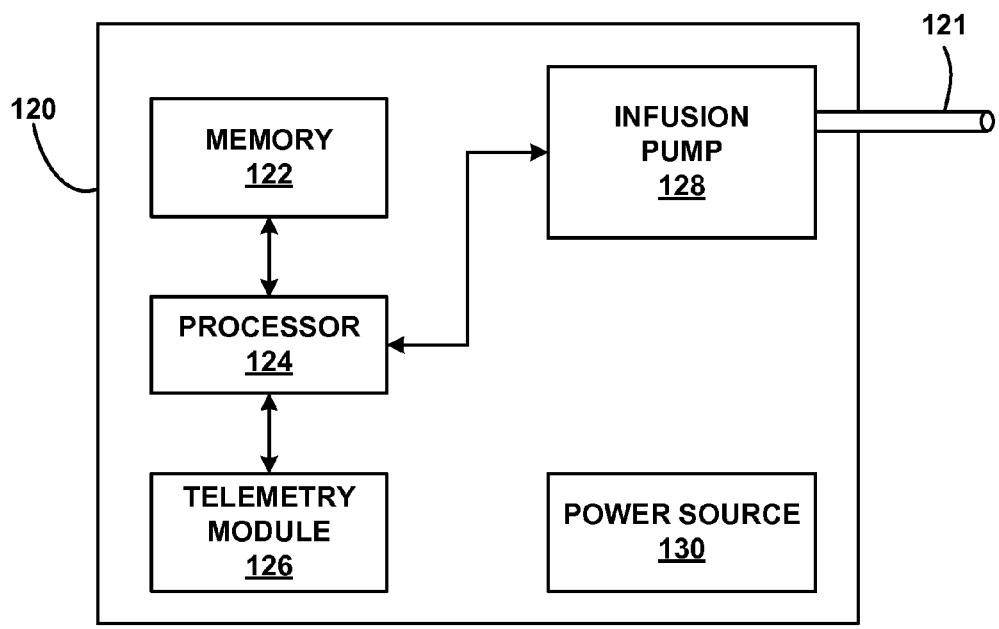
FIG. 9 is a functional block diagram illustrating various components of an implantable fluid delivery device that may be used with a fluid delivery conduit that is implanted via the technique shown in FIG. 5.

FIG. 9 is a functional block diagram illustrating various components of an implantable fluid delivery device 120 for providing delivering a fluid, such as a drug, to occipital region 31 via catheter 121 that is implanted using tools 10 or 100. As shown in FIG. 9, fluid delivery device 120 includes memory 122, processor 124, telemetry interface 126, infusion pump 128, and power source 130. Delivery device 120 may be implanted within patient 36 or located externally on patient 36. Catheter 121 is coupled to infusion pump 128 and implanted within occipital region 31, such as proximate to occipital nerves 77, 78, or 80 or trigeminal nerve 86. Catheter 121 may be implanted within patient 36 using implant tool 10. For example, catheter 121 may be introduced through inner lumen 29 of cannula 24 (not shown in FIG. 9) after cannula 24 is introduced into tissue by any suitable approach, such as the ones described above with reference to FIGS. 6A-C or 7A-D. Accordingly, the lumen 39 of cannula 24 may be sized to accommodate catheter 121. Catheter 121 may be tunneled within patient 36 to an implanted device 120 or tunneled transcutaneously to an external delivery device 120.

Processor 124 controls the amount of drug dispensed by infusion pump 128 to patient 36. Processor 124 may use instructions stored within memory 122 to determine the time, amount, and frequency of drug delivery through catheter 121. Memory 122 may also store data related to the dispensing of drugs by infusion pump 128. Infusion pump 128 may continuously or periodically pump a liquid drug to patient 36. Telemetry interface 126 may communicate with an external program (not shown) to download new delivery instructions or upload delivery data. Power source 130 may include a rechargeable battery or induction coil produce power necessary for operation of fluid delivery device 120.

Figure 10:
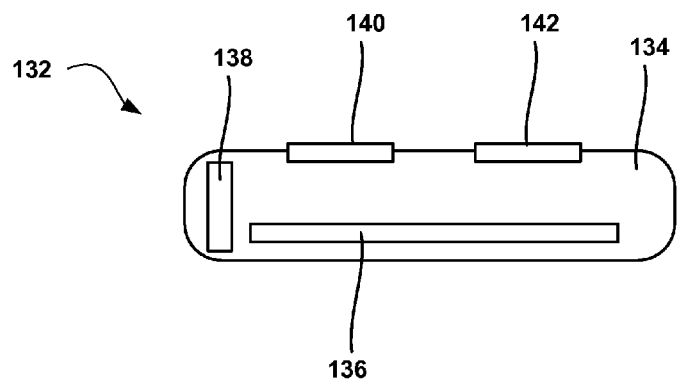
FIG. 10 is a schematic diagram illustrating an exemplary leadless stimulation module for stimulation of an occipital or trigeminal nerve.

Implant tool 10 or 100 may also be used to directly implant a leadless electrical stimulation module within occipital region 31, where the module provides leadless electrical stimulation using a unitary, integrated stimulation module carrying one or more electrodes, stimulation pulse generation circuitry, and optionally telemetry circuitry. FIG. 10 is a schematic diagram illustrating an exemplary leadless electrical stimulation module 132 for electrical stimulation of an occipital nerve 77, 78, 80 or trigeminal nerve 86. Stimulation module 132 may be implanted proximate to the nerve within occipital region 31 using implant tool 10 or 100. Stimulation module 132 includes implantable housing 134, circuit board 136, power supply 138, electrode 140, and electrode 142. Stimulation module 132 contains all necessary components to provide complete stimulation therapy without any lead or other wire connected to stimulation module 132. Stimulation module 132 may be implanted using devices and techniques as described in this disclosure.

Housing 134 is biocompatible and protects the components of stimulation module 132 from corrosive biological fluids and tissues. Housing 134 may contain fixation mechanisms, such as tines similar to tines 42, 44 of leads 34, 35, respectively, to secure stimulation module 132 near a desired nerve location. Circuit board 136 includes components such as a processor, memory, telemetry circuitry, or other electronics necessary for performing electrical stimulation. Power source 138 includes a battery or rechargeable battery to power the electrical circuitry of stimulation module 132. Power source 138 may also generate power through a trickle charger utilizing patient motion or induction with an external device. Electrodes 140 and 142 are attached to housing 134 and may be either a cathode or anode to provide electrical stimulation. In some embodiments, stimulation module 132 may include more than two electrodes. Alternatively, electrodes 140 or 142 may be tethered to housing 134 with a lead. In some embodiments, multiple leadless stimulation modules 132 may be implanted within the pelvic floor using devices and techniques as described in this disclosure.

Figure 11:
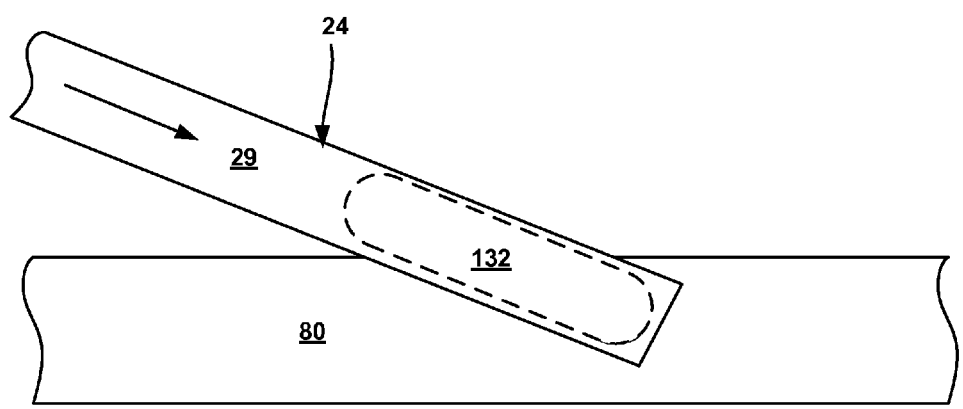
FIG. 11 is a schematic diagram illustrating implantation of the leadless stimulation module of FIG. 10 proximate to an occipital nerve through a cannula.

FIG. 11 is a schematic diagram illustrating implantation of leadless stimulation module 132 proximate to occipital nerve 80 via cannula 24. Occipital nerve 80 is merely one example, and in other embodiments, leadless stimulation module 132 may be implanted proximate to another occipital nerve 77, 78 or trigeminal nerve 86. Inner lumen 144 of cannula 24 may be sized to receive module 132. Stimulation module 132 may be small enough to slide through inner lumen 144 of cannula 24 and implanted within occipital region 31. In other embodiments, stimulation module 132 may be implanted through needle 18 without cannula 24. In some cases, a guide wire or stylet may be used to aid in placing stimulation module 132 in an appropriate location. In addition, more than one stimulation module 132 may be placed adjacent to occipital nerve 80 for effective stimulation therapy.

Many embodiments of the invention have been described. Various modifications may be made without departing from the scope of the claims. These and other embodiments are within the scope of the following claims.

The invention claimed is:

1. A method comprising:
   introducing an implant tool into a patient, the implant tool comprising:

a malleable needle; and a cannula disposed around at least a portion of the needle, wherein the cannula comprises a shape memory material;

advancing the needle to a target tissue site in at least one of a head or a neck of the patient and proximate to at least one of an occipital nerve or a trigeminal nerve of the patient, wherein the needle defines a path through tissue of the patient; and withdrawing the needle from the path, wherein the cannula remains at least partially within the path and changes from a first shape to a second shape after the needle is removed.

2. The method of claim 1, further comprising delivering an electrical test signal to the patient via at least one of the needle or at least one electrode disposed proximate to a distal end of the implant tool.

3. The method of claim 1, further comprising changing a needle shape of the needle.

4. The method of claim 3, wherein changing the needle shape comprises manually manipulating the needle while the needle is at least partially disposed within the patient.

5. The method of claim 3, wherein changing the needle shape comprises manually manipulating the needle to define a substantially curvilinear shape.

6. The method of claim 3, further comprising at least partially withdrawing the needle from the patient prior to changing the needle shape.

7. The method of claim 1, wherein the shape memory material comprises at least one of a copper-zinc-aluminum alloy, copper-aluminum-nickel alloy or a nickel-titanium alloy.

8. The method of claim 1, further comprising introducing a medical device into an inner lumen of the cannula.

9. The method of claim 8, wherein the medical device includes a fluid delivery conduit.

10. The method of claim 8, wherein the medical device includes a stimulation module.

11. The method of claim 8, wherein the medical device comprises an elongated body extending between a proximal end and a distal end, and the method further comprises tunneling the proximal end of the elongated body to a therapy delivery source implant site within the patient.

12. The method of claim 8, wherein the medical device includes an implantable medical lead comprising one or more electrodes.

13. The method of claim 12, wherein the implantable medical lead comprises a first set of electrodes and a second set of electrodes, and advancing the needle to the target tissue site comprises positioning the needle across a midline of the patient, and the method further comprises withdrawing the cannula from the patient to deploy the implantable medical lead into the patient such that the first set of electrodes is positioned on a first side of the midline and the second set of electrodes is positioned on a second side of the midline.

14. The method of claim 8, wherein the medical device is a first medical device, the target tissue site is a first target tissue site, the method further comprising:

advancing the needle to a second target tissue site proximate to a branch of the at least one of the occipital nerve or the trigeminal nerve on an opposite side of a midline of the patient from the first medical device;

withdrawing the needle from the patient; and introducing a second medical device into the inner lumen of the cannula.

15. The method of claim 1, wherein the second shape is substantially curvilinear.

16. The method of claim 1, further comprising positioning the needle and cannula with respect to the at least one of the occipital nerve or the trigeminal nerve such that when the cannula changes to the second shape, the cannula wraps around at least a portion of the at least one of the occipital nerve or the trigeminal nerve.

17. The method of claim 1, wherein advancing the needle to the target tissue site comprises positioning the needle within subcutaneous tissue of the patient superior to the at least one of the occipital nerve or the trigeminal nerve.

18. A method comprising:

introducing an implant tool into a patient via an entry point, the implant tool comprising:

a cannula comprising a shape memory material; and a malleable needle disposed at least partially in an inner lumen of the cannula, wherein a distal tip of the needle extends past a distal end of the cannula;

advancing the distal tip of the needle to a target tissue site in at least one of a head or a neck of the patient and proximate to at least one of an occipital nerve or a trigeminal nerve of the patient, wherein the distal tip of the needle defines a path from the entry point to the target tissue site;

changing a first shape of the needle; and withdrawing the needle from the path, wherein the cannula remains at least partially within the path and changes from the first shape of the needle to a second shape upon withdrawal of the needle from the path.

19. The method of claim 18, wherein introducing the implant tool into the patient comprises introducing the needle and the cannula superior to a fascia layer.

20. The method of claim 18, wherein advancing the distal tip of the needle to the target tissue site comprises advancing the distal tip of the needle to position the needle and cannula transversely across the occipital nerve.

21. The method of claim 18, wherein advancing the distal tip of the needle to the target tissue site comprises advancing the distal end of the needle to position the needle and cannula transversely across a brow line of the patient.

22. The method of claim 18, wherein the entry point is within approximately five inches of an ear of the patient.

23. A method comprising:

introducing an implant tool into a patient superior to a fascia layer, the implant tool comprising:

a cannula comprising a shape memory material; and a malleable needle disposed at least partially in an inner lumen of the cannula, wherein a distal tip of the needle extends past a distal end of the cannula;

advancing the distal tip of the needle to a target tissue site in at least one of a head or a neck of the patient and proximate to at least one of an occipital nerve or a trigeminal nerve of the patient, wherein the distal tip of the needle defines a path through tissue of the patient;

withdrawing the needle from the path, wherein the cannula remains at least partially within the path and changes from a first shape to a second shape upon withdrawal of the needle from the path; and introducing a medical device into the cannula.

* * * * *